United States Patent
Osypka et al.

(10) Patent No.: US 10,349,901 B2
(45) Date of Patent: Jul. 16, 2019

(54) SHOCK PROBABILITY DETERMINATION SYSTEM AND METHOD

(71) Applicant: Osypka Medical GmbH, Berlin (DE)

(72) Inventors: Markus J. Osypka, La Jolla, CA (US); Clemens Feige, Berlin (DE); Marcel D. Gestewitz, Berlin (DE); Florin-Viorel Petrov, Berlin (DE); Yasser A. Nassef, Dubai (AE)

(73) Assignee: OSYPKA MEDICAL GMBH, Berlin (DE)

( * ) Notice: Subject to any disclaimer, the term of this patent is extended or adjusted under 35 U.S.C. 154(b) by 357 days.

(21) Appl. No.: 15/234,953

(22) Filed: Aug. 11, 2016

(65) Prior Publication Data

US 2017/0053077 A1 Feb. 23, 2017

Related U.S. Application Data

(60) Provisional application No. 62/207,599, filed on Aug. 20, 2015.

(51) Int. Cl.
*A61B 5/021* (2006.01)
*A61B 5/01* (2006.01)
(Continued)

(52) U.S. Cl.
CPC .............. *A61B 5/7278* (2013.01); *A61B 5/01* (2013.01); *A61B 5/029* (2013.01);
(Continued)

(58) Field of Classification Search
CPC ..... A61B 5/7278; A61B 5/01; A61B 5/02028; A61B 5/02055; A61B 5/02108;
(Continued)

(56) References Cited

U.S. PATENT DOCUMENTS 5,551,435 A 9/1996 Sramek
5,584,298 A 12/1996 Kabal
(Continued)

FOREIGN PATENT DOCUMENTS

WO 2002078539 A1 10/2002
WO 2012085750 A1 6/2012
WO 2013003787 A2 1/2013

OTHER PUBLICATIONS

International Search Report and Written Opinion of International Patent Application No. PCT/EP2016/069718 dated Dec. 2, 2016 in 14 pages.
(Continued)

*Primary Examiner* — Navin Natnithithadha
(74) *Attorney, Agent, or Firm* — Procopio Cory Hargreaves and Savitch LLP

(57) ABSTRACT

A shock probability determination system and method provides an output of probabilities for different types of shock based on input of selected patient demographic parameters and current clinical parameter values as well as normal ranges for each clinical parameter based on patient demographic data. The probability of different types of shock is determined based on comparison of current clinical parameter values of selected patient hemodynamic parameters to a normal range for each hemodynamic parameter. In one aspect, probabilities of cardiogenic shock, hypovolemic shock, septic shock, and anaphylactic shock are determined. In another aspect, a fluid status indicator is determined based on real-time probability of hypovolemic shock.

5 Claims, 15 Drawing Sheets

(51) Int. Cl.
  A61B 5/029    (2006.01)
  A61B 5/0295   (2006.01)
  G16H 50/30    (2018.01)
  G16H 50/20    (2018.01)
  A61B 5/00     (2006.01)
  G06F 19/00    (2018.01)
  A61B 5/02     (2006.01)
  A61B 5/08     (2006.01)
  A61B 5/0205   (2006.01)

(52) U.S. Cl.
  CPC ...... *A61B 5/02028* (2013.01); *A61B 5/02055* (2013.01); *A61B 5/0295* (2013.01); *A61B 5/02108* (2013.01); *A61B 5/0816* (2013.01); *A61B 5/7225* (2013.01); *A61B 5/7264* (2013.01); *A61B 5/7275* (2013.01); *G06F 19/3418* (2013.01); *G16H 50/20* (2018.01); *G16H 50/30* (2018.01); *A61B 5/021* (2013.01); *A61B 5/02007* (2013.01); *A61B 5/743* (2013.01)

(58) Field of Classification Search
  CPC ..... A61B 5/029; A61B 5/0295; A61B 5/0816; A61B 5/7225; A61B 5/7264; A61B 5/7275; A61B 5/02007; A61B 5/021; A61B 5/743; G16H 50/30; G16H 50/20; G06F 19/00; G06F 19/3418
  USPC .......................................... 600/481, 483, 526
  See application file for complete search history.

(56) References Cited

U.S. PATENT DOCUMENTS

| | | | | |
|---|---|---|---|---|
| 5,865,758 | A * | 2/1999 | Louzianine | ............ A61B 5/024 600/485 |
| 6,280,390 | B1 * | 8/2001 | Akselrod | ........... A61B 5/02416 600/475 |
| 6,776,764 | B2 | 8/2004 | Pinsky | |
| 8,246,546 | B2 * | 8/2012 | Huiku | ..................... G06F 19/00 600/483 |
| 9,332,911 | B2 | 5/2016 | Parlikar et al. | |
| 2008/0001735 | A1 | 1/2008 | Tran | |
| 2008/0287753 | A1 | 11/2008 | Parlikar et al. | |

OTHER PUBLICATIONS

Berger, Tony et al. (2012): Shock index and early recognition of sepsis in the emergency department: Pilot study. Western Journal of Emergency Medicine, vol. XIV, No. 2 : Mar. 2013, 168.

Rady, Mohamed Y (2005): Bench-to-bedside review: Resuscitation in the emergency department. Critical Care Apr. 2005, 9, 2, 170-176.

BMJ Best Practice (last updated; Oct. 4, 2013); Assessment of shock; Step-by-step diagnostic approach. http://bestpractice.bmi.com/best-oractice/monoRraoh/779.html.

University of Pennsylvania School of Veterinary Medicine: How can hypovolemic shock be differentiated from the other two forms of shock? Available on the Internet (Oct. 7, 2014) at htto://cal.vet.uoenn.edu/proiects/saRastro/case6/tvoeshck.htm.

Mayo Clinic (Rochester, MN): For medical professionals: for patients in shock, recognition, rapid treatment are key (case study). Available on the Internet (Oct. 7, 2014)at htto://www.mavoclinic.orR/medical-orofessionals/clinical-updates/trauma/patients-in-shock-recoRnition-raoid-treatment-kev?o=1.

Michard F, Lopes MR, Auler JOC (2007): Pulse pressure variation: beyond the fluid management of patients with shock (Commentary). htto://www.ccforum.com/content/ll/3/131.

Normal Hemodynamic Parameters, Aug. 2015, by LIDCO, www.lidco.com/clinical/hemodynamic.php.

* cited by examiner

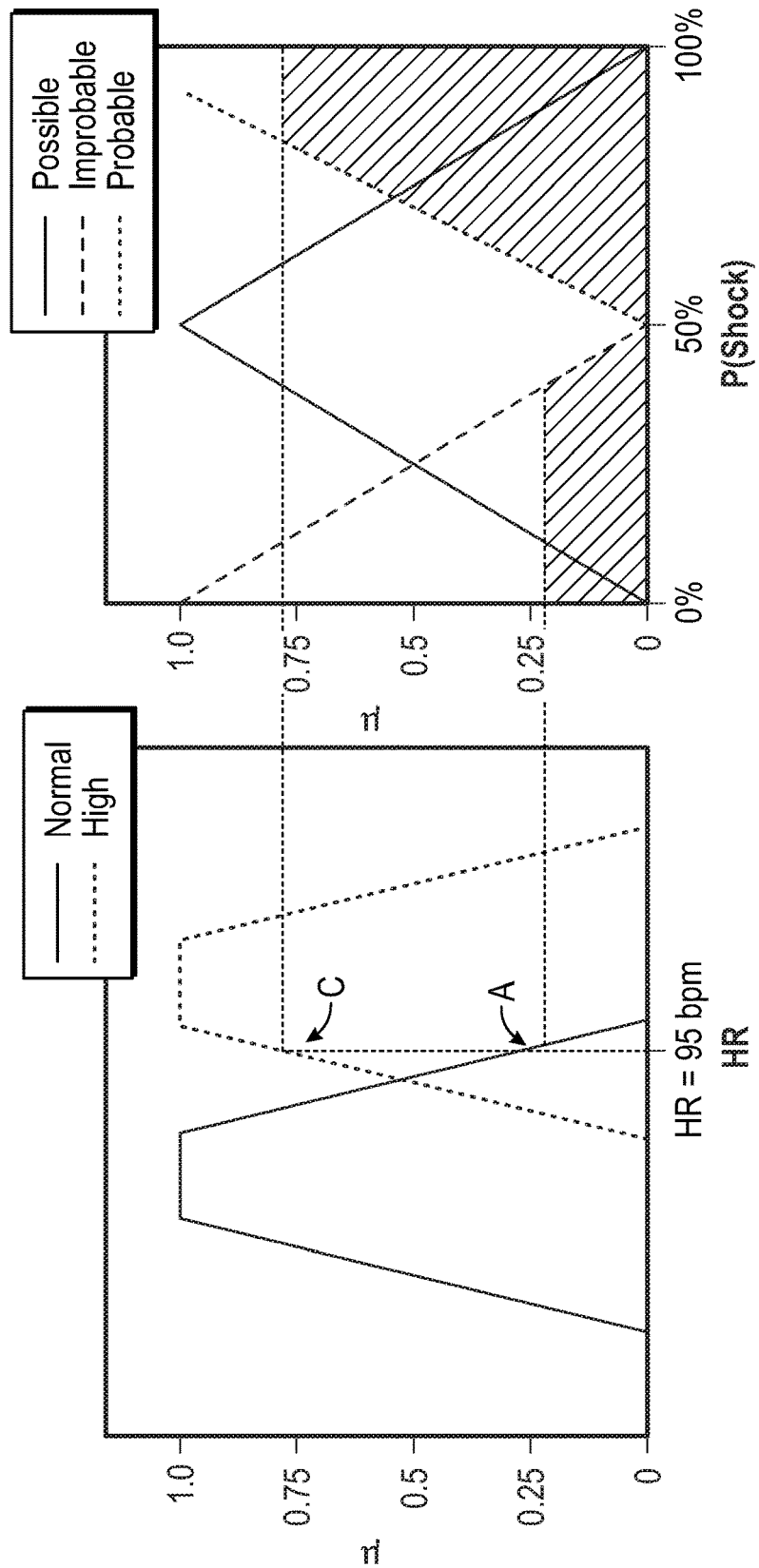

SHOCK PROBABILITY DETERMINATION SYSTEM AND METHOD

CROSS REFERENCE TO RELATED APPLICATIONS

This application claims the benefit of priority under 35 U.S.C. § 119(e) of U.S. Provisional Patent Application No. 62/207,599 filed on Aug. 20, 2015, the contents of which are incorporated herein by reference.

BACKGROUND

1. Field of the Invention

This invention relates generally to a method and system for evaluating a patient for shock, and specifically concerns a method and system for automatically determining probabilities of one or more shock types based on patient clinical and hemodynamic data.

2. Related Art

Shock is a life threatening situation which requires immediate attention and care. A wide range of illnesses can lead to shock. Shock can cause multiple organ failure. It can lead to life-threatening complications, such as heart failure. Therefore it is critical that the underlying illness, defining the type of shock, is determined and treated as quickly as possible.

Hemodynamically, all shock types are characterized by very low blood pressure and rapid heart rate. Other symptoms are, but not limited to, mental confusion, cool skin and rapid shallow breathing. Most shock cases can be classified into four major types: cardiogenic shock, hypovolemic shock, septic shock, and anaphylactic shock.

Cardiogenic shock is caused by heart malfunction or problem, which leads to inability to eject enough blood for the body needs. Cardiogenic shock is sometimes referred to as obstructive shock.

Hypovolemic shock is mainly due to massive blood loss or loss of body fluids, which, for instance, is caused by injury and subsequent bleeding, or sun stroke especially in elderly people.

Septic shock is the most critical type of shock. Bacteria are entering the blood stream, which leads to sepsis. Septic shock occurs when bacteria and their toxins damage tissues or organs in the body. Septic shock is equivalent to systemic inflammatory response syndrome (SIRS) secondary to a documented infection and describes a wide spectrum ranging from sepsis to severe sepsis to septic shock and multiple organ dysfunction syndrome (MODS).

Anaphylactic shock is caused by an allergic reaction of the body.

Each shock type requires a particular treatment. Mixed hemodynamic patterns of shock patients make classification of their shock type difficult, even more when considering a patient's life-threating condition and the limited time left to apply the right therapy. Traditionally, the differentiation of shock is performed by clinical assessments and investigations which are time consuming.

Rady [Mohamed Y. Rady: Bench-to-bedside review: Resuscitation in the emergency department". Critical Care April 2005, 9, 2, 170-176] describes the challenge of assigning a patient in shock based on the plurality of hemodynamic parameters preload, filling pressures, end-diastolic volumes, cardiac output, afterload, systemic vascular resistance, systemic oxygen delivery, systemic oxygen consumption, systemic oxygen extraction ratio and global oxygen balance $SVO_2$ or $SCVO_2$.

Some of the shock types do not require comprehensive measurement of hemodynamic parameters because the reason for the shock is obvious. For instance, an injured patient exhibiting serious bleeding due to an accident is likely to develop a hypovolemic shock if not treated properly. For many acute illnesses, however, shock differentiation is more difficult. Clinical circumstances, such as lack of time or manpower, time consuming investigations or limited medical expertise can cause a delay or incorrect diagnosis and treatment which ultimately results in death.

The ratio of heart rate to systolic blood pressure has been described as the shock index, with a normal range of 0.5 to 0.7 in normal adults. It is used mostly to confine hypovolemic shock and it is not applicable in septic and cardiogenic shock, when heart rate is always increased in response to other factors.

The University of Pennsylvania, School of Veterinary Medicine has established a website on the Internet disclosing a technique for differentiating hypovolemic shock from the other types of shock. The suggested evaluation refers to review of the history, undertaking a complete physical exam, determination of external fluid loss (for instance, vomiting or blood loss) or internal fluid loss (for instance, fluid accumulation, internal bleeding), auscultation of the heart, evaluation of pulse quality and rhythm, ECG, chest X-Rays and evaluation for any evidence of infection, history of trauma, hypoxia, pancreatitis, burns or immunosuppression. These examinations and evaluations require time which is always a critical factor for shock patient, in particular in an emergency department which may be the first in line dealing with a shock patient.

U.S. Pat. No. 5,551,435 to Sramek discloses a method and system for therapeutic management relying on the patient's mean arterial blood pressure and stroke volume index but does not differentiate in any way between different shock conditions.

U.S. Pat. No. 6,776,764 to Pinsky discloses a method and apparatus for optimizing treatment of hemodynamically unstable patients based on measurements of arterial pressure and stroke volume of the patient and subsequent calculation of stroke volume variation, pulse pressure variation, mean arterial pressure, elastance and cardiac power. The method comprises treatment of the patient, including the administration of fluid infusions, vasoactive drugs or inotropic drugs. U.S. Pat. No. 6,776,764 references other patents related to this art which are incorporated by reference (U.S. Pat. Nos. 5,551,435; 5,584,298; 5,865,758; 6,280,390).

Assessment and differentiation of shock is a complex undertaking which usually requires rapid treatment. All aforementioned methods and apparatuses take a step-by-step approach to determine the type of shock.

SUMMARY

In one aspect, a shock probability determination system is provided for shock differential diagnosis, which comprises at least one hardware processor and one or more executable software modules that, when executed by the at least one hardware processor, determine the probability of one or more types of shock based on a combination of current values of selected patient physiological or vital parameters such as cardiac, hemodynamic, respiratory, body temperature and the like. In one aspect, a group of selected vital parameters are monitored or determined along with patient demographic data and the input value of each parameter is compared to the normal range for that parameter based on input or stored patient demographic data (e.g. age, gender, body mass or weight, height). In one aspect, the results of this comparison are used to determine and continuously monitor probability of at least one type of shock. In another aspect, probabilities of different types of shock (cardiogenic, hypovolemic, septic or anaphylactic) are determined and compared to determine a most likely shock type. In one aspect, the selected parameters may be monitored and the shock probabilities for one shock type or all different shock types may be determined at predetermined intervals or on an on-going basis, and in one aspect the trends in shock probability may be displayed on an output monitor in the form of a trend graph. This allows the physician to determine whether therapy is going in the right direction.

In a shock type differentiation system, the different shock probabilities may be determined based on selected groups of hemodynamic and other parameters which may the same or different for different shock types, in particular, but not limited to, heart rate, stroke volume, cardiac output, mean arterial blood pressure, predictors of fluid responsiveness such as stroke volume, stroke volume variation, pleth variability index and pulse pressure variation, cardiac contractility or index of contractility, cardiac output, thoracic fluid content, flow time, systolic time ratio, systemic vascular resistance, temperature, respiration rate, ventilation rate, or a subset of the foregoing values, or a combination of such patient hemodynamic values and further parameters derived from such values, such as sample entropy and other statistical measures, and the patient's demographic data (i.e., gender, age, body mass or weight, height). Other parameters which may be incorporated may be based on blood tests, organ failure, or the medical history of the patient. Respective software modules are configured to calculate probability of generic shock, cardiogenic shock, hypovolemic shock, septic shock, and anaphylactic shock, respectively.

In one aspect, one or more processing units or modules determine the normal or normalized ranges of hemodynamic parameters based on the patient's demographic data. In one aspect, for hemodynamic parameters which are related to or derived from blood flow, normalized ranges for adults can be determined considering a 'normal' cardiac index CI (BSA) of 3.5 L/min/m$^2$. If needed, the 'normal' cardiac index can be adjusted or tailored based on the patient's age, gender, and size (body surface area or body mass and height). For example, a normal cardiac index CI (BM) for neonates and very small children is 200-240 ml/min/kg. A postoperative goal for CI (BSA) is around 4.5 L/min/m$^2$. For each hemodynamic parameter, ranges can be established by applying limits of a predetermined percentage calculated from the determined range center, for example +/−20%.

Shock differentiation processing units determine the likelihood or probability of each type of shock based on the comparison of current clinical parameter values in the selected group of clinical parameters for the respective shock type to the normal ranges for the respective clinical parameters in the selected group, and a weighting factor is applied to the probability determination for each clinical parameter depending on its importance in determining the probability of a respective type of shock. In one embodiment, the current clinical parameter values are input to algorithms employing fuzzy logic in order to determine the likelihood for each shock type. In an alternative embodiment, a neural network method can be implemented in place of the fuzzy logic method.

In some embodiments, a generic shock probability (probability of shock of any type) is first determined based on identification of very low blood pressure or hypotension (MAP or mean arterial pressure) associated with high heart rate (HR). Once it is confirmed that the chance of some type of shock (generic shock) is probable (high or very high HR together with lower or very low MAP), the probabilities for different types of shock are determined based on combinations of clinical parameter values which deviate outside the normal range for the particular patient. In some embodiments, if generic shock is determined to be improbable (normal or low HR combined with normal or higher MAP), no further shock type processing is carried out. In one embodiment, numeric probabilities for generic shock are determined if shock is in a probable or possible range based on deviation of HR and MAP outside the normal ranges, and these probabilities are used to restrict or reduce some or all of the probabilities for specific types of shock.

A display unit receives the output of the shock differentiation processing unit and displays the likelihoods or probabilities for each shock type to provide the medical professional with an orientation towards shock differentiation. In one embodiment, a filter step may be included to identify one shock type as the most likely shock type or final result of the shock differentiator.

In one embodiment ('off-line'), the patient's hemodynamic parameters are obtained by one or more measurement techniques, the results of which are entered into the system. This embodiment is suitable for use when accessing the shock probability determination system though a website or via a computer program or application on a smart phone.

In other embodiments, the shock probability determination system is connected to outputs of a hemodynamic monitor ('real-time'), or the system may be incorporated in the hemodynamic monitor itself. The hemodynamic monitor is connected to a patient and obtains all or a portion of the hemodynamic parameters and feeds those automatically into the shock probability determination system.

In another aspect, a method using at least one hardware processor is provided for determining the probability of different types of shock, in which a patient's clinical and demographic parameters are used to determine the normal range for each clinical parameter based on the patient's demographic data. Current clinical parameter values are compared to the normal range for each hemodynamic parameter and the likelihood or probability of each type of shock is then determined, using algorithms employing fuzzy logic or a neural network method in order to determine the probability for each shock type.

A display unit receives the output of the shock probability processor and displays the likelihoods or probabilities for each shock type to provide the medical professional with an orientation towards shock differentiation. The shock probabilities may be displayed as one or more of a numeric output, a bar chart, a trend graph over time, and the like.

In another aspect, non-transitory computer-readable medium has one or more sequences of instructions stored therein, wherein the one or more sequences of instructions, when executed by a processor, cause the processor to: determine the normal ranges of clinical parameters based on the patient's demographic data, receive current clinical values and compare the received clinical parameter values to the normal range for each clinical parameter, and determine the likelihood or probability of each type of shock based on the comparison using algorithms employing fuzzy logic or a neural network method in order to determine the likelihood for each shock type.

In another aspect, in a computer implemented method of determining shock probabilities for a plurality of shock types, one or more computing devices comprising data storage and a hardware processor are programmed to perform steps comprising receiving input of a plurality of currently measured values of selected patient clinical parameters comprising at least hemodynamic parameters, comparing each clinical parameter to a normal range for that parameter based on determined or stored patient demographic data and using the comparison to determine probabilities of a plurality of shock types comprising cardiogenic shock, hypovolemic shock, septic shock, and anaphylactic shock. In one embodiment, the one or more computing devices are programmed to perform steps of processing a first group of selected clinical parameters to determine individual probabilities of cardiogenic shock for each of the selected clinical parameters in the first group, where the individual parameter based probabilities are based on the respective comparison of each of the respective individual clinical parameter values of the first group to the normal range for that parameter; process a second group of selected clinical parameters to determine individual probabilities of hypovolemic shock for each of the selected clinical parameters in the second group, where the individual parameter based probabilities are based on comparison of each of the respective individual clinical parameter values of the second group from the normal range for that parameter; processing a third group of selected clinical parameters to determine individual probabilities of septic shock for each of the selected clinical parameters in the third group, where the individual parameter based probabilities are based on the comparison of each of the respective individual clinical parameter values of the third group from the normal range for that parameter; and processing a fourth group of selected clinical parameters to determine individual probabilities of anaphylactic shock for each of the selected clinical parameters in the fourth group, where the individual parameter based probabilities are based on the respective comparisons of each of the respective individual clinical parameter values of the fourth group to the normal range for that parameter. A weighting is assigned for each of the determined individual parameter based probabilities in each group, and the weighted individual parameter based probabilities in the respective groups are separately combined to determine probabilities of cardiogenic shock, hypovolemic shock, septic shock, and anaphylactic shock, respectively.

In one aspect, at least some of the shock probabilities are adjusted based on one or more other probabilities to obtain restricted shock probabilities. The resultant shock probabilities are displayed on an output display unit. Each group of clinical parameters may include one or more of different clinical parameters or different clinical parameter weightings from the other three groups. In one aspect, the first and second groups of parameters comprise index of contractility (ICON), systemic vascular resistance (SVR), stroke volume (SV), systolic time ratio (STR), thoracic fluid contact (TFC) and one of stroke volume variability (SVV), pleth variability index (PVI™), pulse pressure variation (PPV), or corrected flow time (FTc), the third group of parameters comprises SVR, cardiac output (CO), ICON, TFC, and one of SVV, PVI, PPV, or FTc, and the fourth group of parameters comprises SVR, CO and TFC. Corrected flow time or FTc is the flow time normalized for heart rate. Other combinations of patient clinical parameters may be selected in alternative embodiments.

In one aspect, a generic shock probability M (generic shock condition "improbable") is determined using at least two selected clinical parameters indicative of any type of shock condition being present, and computing a restricted probability of specific shock types if M(generic shock condition "improbable") is greater than zero according to the following:

$$P^*(\text{shock type}) = P(\text{shock type}) * (1 - M(\text{generic shock condition, 'improbable'})),$$

where $P^*$(shock type)=restricted shock probability due to a generic shock condition 'improbable', and P(shock type)= determined probability of shock type cardiogenic, hypovolemic, septic, or anaphylactic prior to generic shock restriction. One of the shock types may have a first shock probability which is not restricted based on probability of any other shock type other than a generic shock condition 'improbable' which is greater than zero, and the other shock types each have a shock probability which is restricted based on the probability of one or more other shock types and the generic shock condition 'improbable' if greater than zero.

In one aspect, predetermined shock types have a restricted shock probability determined by based on the highest probability of two or more other considered shock types, using the relationship:

$$P'(\text{shock type}) = P^*(\text{shock type}) * (1 - \max M(\text{other shock type, 'probable'})),$$

where P'(shock type) is the restricted probability of the respective shock type based on other shock type probabilities, and max M(other shock type, 'probable') is shock condition probability 'probable' having the highest value among the two or more other considered shock types.

In one aspect, the generic shock probability is determined based on the clinical parameters of heart rate and mean arterial blood pressure.

The system and method provides a systematic and fast recommendation for a differential diagnosis of shock.

In another aspect, a system for determining and monitoring a patient's fluid status on an ongoing basis comprises at least one hardware processor and one or more executable software modules that, when executed by the at least one hardware processor, determine an unrestricted probability of hypovolemic shock P(shock$_{hypovolemic}$), determine a fluid status indicator FluidDx indicative of blood volume from the following relationship: FluidDx=1−P(shock$_{hypovolemic}$). This system may be incorporated in a shock probability determination and differentiation system for determining probabilities of other types of shock in addition to hypovolemic shock, with a separate fluid status indicator provided as an output or displayed on an output display unit in any format, such as numeric, a bar chart, or a trend graph. Alternatively, a stand-alone fluid status monitoring unit or system may be provided for use in fluid management of any patient, not only patients undergoing emergency evaluation for shock. If the probability of hypovolemic shock is very low, then the fluid status is high, which means that high blood volume conditions which require treatment may be present. Alternatively, if the probability of hypovolemic shock is high or very high, then the fluid status or blood volume is low, and the physician may supply fluid to a patient while monitoring the change in fluid status until a normal blood volume is reached.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 8 illustrates implementation of two linguistic rules for probability of a general shock condition;

FIG. 9 illustrates the defuzzification of fuzzified heart rate values;

DETAILED DESCRIPTION

Certain embodiments as disclosed herein provide for a system and method for automatic determination of probabilities of different types of shock from a patient's hemodynamic or other clinical data and demographic data. The system may be incorporated in or associated with a real-type patient hemodynamic data monitor, or may be provided as a mobile phone or computer application or a website accessible by medical personnel to enter or transmit current patient data and receive an output of determined shock type probabilities. Embodiments disclosed herein also provide for a system and method for monitoring a patient's blood volume and providing a fluid data indicator output which is based on probability of hemodynamic shock.

After reading this description it will become apparent to one skilled in the art how to implement the invention in various alternative embodiments and alternative applications. However, although various embodiments of the present invention will be described herein, it is understood that these embodiments are presented by way of example only, and not limitation.

Figure 1:
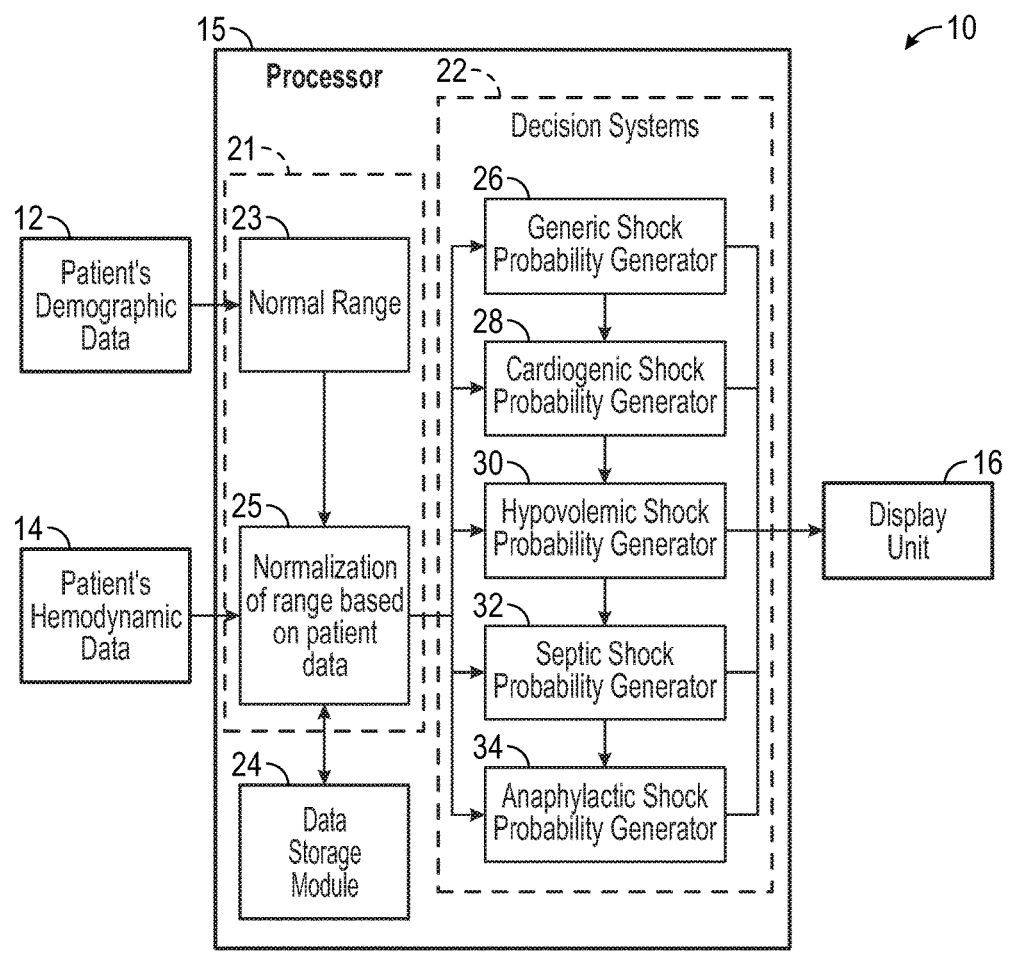
FIG. 1 is a block diagram of one embodiment of a shock differentiation system for determining probability of different shock types based on input of patient demographic and hemodynamic or other clinical data.
Figure 2:
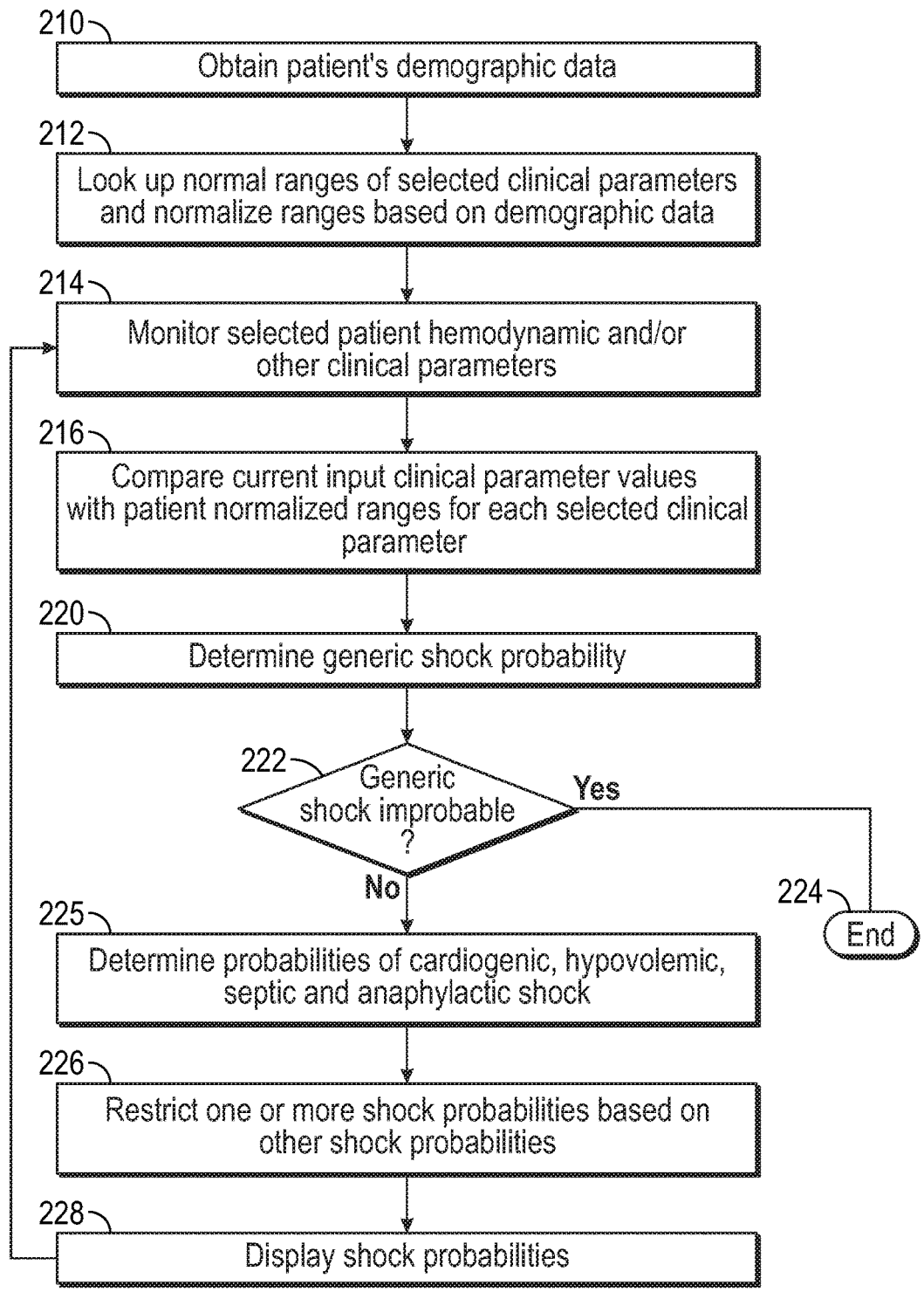
FIG. 2 is a flow diagram illustrating steps of a method for determining probability of different shock types in the system of FIG. 1.

One embodiment of a system and method for evaluating probabilities of different shock types is illustrated in FIGS. 1 and 2. System 10 of FIG. 1 comprises a computer or processor 15 having an input 12 for receiving a patient's demographic data (age, gender, body mass or weight, and height), one or more inputs 14 for receiving clinical data such as hemodynamic or other clinical data, and an output display unit or module 16 which displays probabilities of cardiogenic, hypovolemic, septic, and anaphylactic shock. In one embodiment, clinical data may be manually entered at input 14 by a clinician, and in some embodiments only one input may be provided for entry of both demographic and clinical data. Alternatively, demographic data may be obtained automatically from a patient's on line health records. In one embodiment, input 14 may be connected to the output of a hemodynamic monitor for collecting real time patient data, as described in more detail below in connection with FIG. 14.

The hemodynamic assessment of a patient requires consideration of a spectrum of clinical or hemodynamic parameters, some of which are somewhat variable in context with the age, gender, body mass (weight) and height of the patient. Based on the hemodynamic assessment, the decision system provides probabilities that the patient is suffering from cardiogenic, hypovolemic, septic or anaphylactic shock. A solely Boolean approach applied to hemodynamics, i.e., a true and false or yes and no decision system, would be complex and because of that most likely prone to errors.

As illustrated in FIG. 1, at least one hardware processing unit or processor 15 includes one or more executable software modules that are executed by the at least one hardware processor. As illustrated in FIG. 1, processor 15 basically comprises a data processing/normalization module 21 and a shock type differentiation module 22. The data processing module includes a first module 23 which determines normal ranges for hemodynamic data for the patient, for example using tables of normal ranges for certain parameters based on age and gender. The range may be normalized by normalization module 25 based on the input 12 of demographic data. As noted above, demographic data may be directly input by medical staff at the scene, or may be retrieved from the patient's online medical records. The processor 15 also includes one or more data storage modules 24 which may store data such as tables of normal ranges of hemodynamic or other clinical values or parameters for patients of different ages, weights, gender, height, or the like, in addition to collected hemodynamic and other clinical parameters for a patient and determined shock probabilities. In one embodiment, the normal range determining module 23 determines the ranges of hemodynamic parameters or other clinical values based on the patient's demographic data. The normal range determined by module 23 is input to a normalization module 25 which normalizes or tailors the normal range based on a therapeutic goal and/or the subject's body mass or weight, height, age and gender.

In clinical practice, therapeutic goals (TG) for various parameters are defined by physicians, and can be tailored towards a patient's size. For hemodynamic parameters which are related to or derived from blood flow, normal ranges for an adult can be determined considering a 'normal' or therapeutic goal cardiac index of 3.5 L/min/m$^2$. The 'normal' cardiac index can be adjusted based on patient demographic data or other conditions based on a therapeutic goal (TG). Thus, for a postoperative patient, a therapeutic goal for a cardiac index might be 4.5 L/min/m$^2$. These adult therapeutic goals are based on body surface area (BSA). For neonates or very small pediatric patients, cardiac index is specified for body mass or weight, and a typical TG or value for such patients is 200-240 ml/min/kg. For each hemodynamic parameter, ranges can be established by applying limits of a predetermined percentage calculated from the determined range center or therapeutic goal, for example +/−20%.

The normalized range for each hemodynamic parameter to be used in the shock evaluation along with the current measured value for that parameter are input to the shock type differentiation module 22 which includes a generic shock probability determining module 26 and four shock probability determining modules or units 28, 30, 32 and 34 which are programmed to calculate shock probabilities for different types of shock based on rules explained in more detail below. Generic shock probability determining module 26 determines an overall or generic shock probability, i.e. probability of any of the four different types of shock. In one embodiment, the shock probability determining modules use fuzzy logic in the probability determination, as described in more detail below in connection with FIGS. 5 to 13, but in other embodiments neural network methods or software including algorithms for determining probability may be used in place of fuzzy logic. In the illustrated embodiment, the cardiogenic shock determining module 28 determines probability of cardiogenic shock based on the currently measured cardiac parameters for the patient and the normalized ranges for each parameter, using a weighting for each parameter. The hypovolemic shock determining module 30 determines probability of hypovolemic shock based on the same parameters as module 28, and also based on the probability of cardiogenic shock as determined by module 28. The septic shock determining module 32 determines probability of septic shock based on the same parameters as modules 28 and 30, and also based on the determined probabilities of cardiogenic shock and hypovolemic shock. The anaphylactic shock determining module 34 determines probability of anaphylactic shock based on same normalized patient data as modules 28, 30, and 32, and also based on the determined probabilities of the other three shock types (i.e. whichever has the highest probability), as described in more detail below.

The probability of different types of shock is based on a combination of current values of patient hemodynamic or other vital or clinical parameters (in particular, but not limited to, stroke volume, predictors of fluid responsiveness such as stroke volume variation, pleth variability index and pulse pressure variation, cardiac contractility, thoracic fluid contents, systolic time ratio and systemic vascular resistance, or a subset of them), and the patient's demographic data (i.e., gender, age, body mass or weight, height).

FIG. 2 is a flow diagram illustrating one embodiment of a method implemented on processor 15 for determining shock probabilities. In step 210, demographic data for a patient in emergency care or in a hospital is obtained either directly or from patient records. In step 212, normal ranges of selected clinical parameters for each shock type are looked up in a local or remote data base, and normalized ranges based on the patient demographic data are selected. In step 214, selected clinical parameters (such as hemodynamic parameters alone or hemodynamic and other variable clinical parameters) of the patient are measured or monitored continuously with suitable patient monitoring equipment. In step 216, current input patient clinical parameters or data are compared with patient normalized ranges for the selected clinical parameter for that patient as determined in step 212. In step 220, a generic shock probability is determined (probability of any type of shock) as described in more detail below with reference to FIG. 11. If the generic shock probability determination indicates that the probability of any shock condition is improbable (step 222), the process ends at step 224 since the likelihood of any type of shock being present is very low. If the generic shock probability is in the range of possible or probable, probabilities for different shock types are determined (step 224) and some shock types are restricted based on one or more other shock types (step 225) as described in more detail below in connection with FIGS. 5 to 13. The resultant shock probabilities are than displayed on an output display unit or monitor 16 (step 228). In one embodiment, the displayed shock probabilities are updated over time as the patient is treated, using the monitored patient clinical data of step 214. If treatment is effective, the generic shock probability should decrease until generic shock is found to be improbable in step 220, and the shock determination procedure then ends (step 224).

The shock differentiation system or module 22 in one embodiment of the invention incorporates a logic relying on 'degrees of truth', also referred to as fuzzy logic or a fuzzy system. In one embodiment, the fuzzy logic decision system employs the following rules for which natural language or linguistic terms are used:

Rule 1: The outcome of the decision system for generic shock or a specific shock condition is classified as "improbable", "possible", or "probable".

Rule 2: A clinical or hemodynamic parameter value can be classified as 'very low', 'low', 'normal', 'high' or 'very high' compared to a normal value for that parameter.

Rule 3: Further differentiation for clinical parameter values is employed by terms like 'increased' (assuming values between normal and high) and 'decreased' (assuming values between normal and low).

The foregoing fuzzy classifications or rules can be modified in other embodiments, and one or more additional fuzzy classifications may be added, such as "very possible" or "slightly low".

Several conditions can be connected with AND/OR/XOR (exclusive OR), and NOT (negation) may also be included. Optionally, each conclusion can be weighted.

Figure 3:
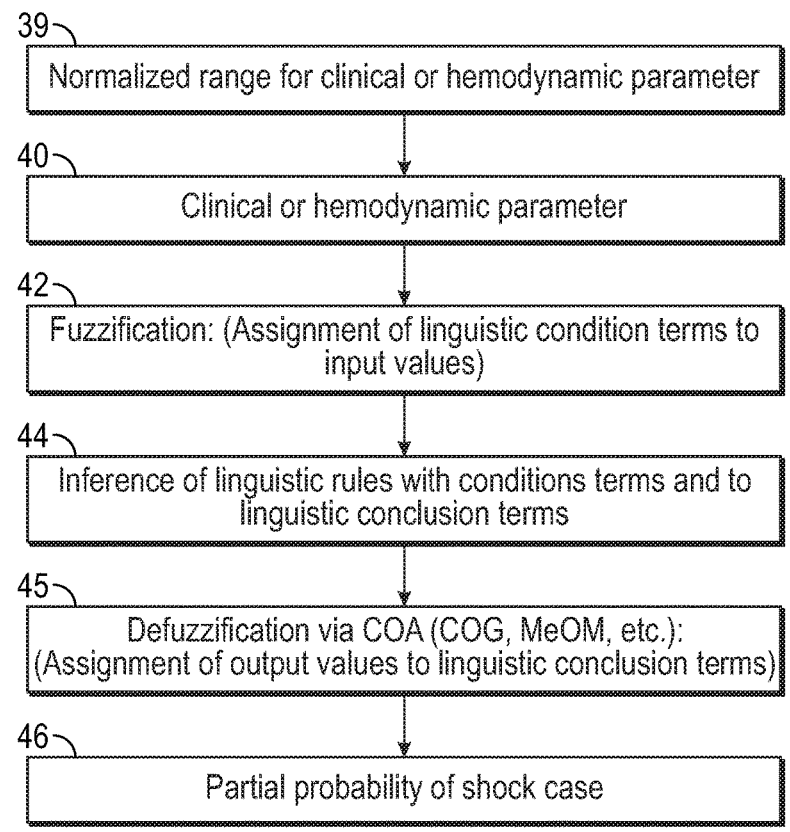
FIG. 3 is a flow diagram illustrating steps of a fuzzification process which transforms normalized input parameter values of FIG. 1 to linguistic terms.

FIG. 3 illustrates the basic steps for implementation of a rule-based fuzzy system to determine partial probability of a type of shock:

Step 39: Determining normalized range around a therapeutic goal (TG) for each clinical or hemodynamic parameter to be used in determining a shock type (see data normalization module 21 of FIG. 1).

Step 40: Input of clinical or hemodynamic parameter.

Figure 5:
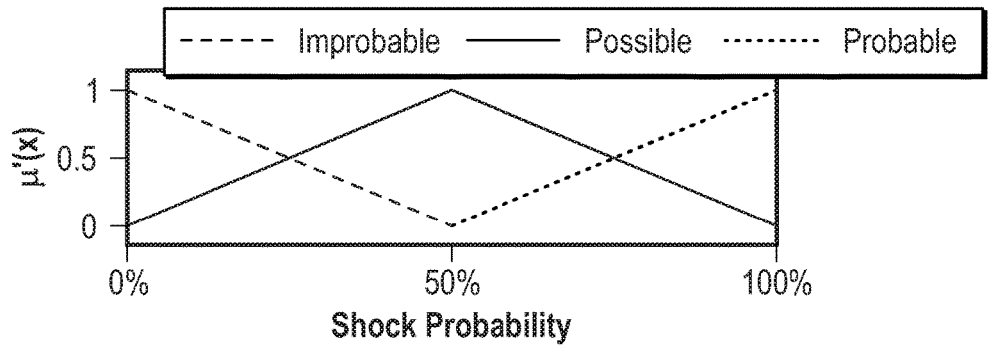
FIG. 5 illustrates assignment of three linguistic conclusion terms (improbable, possible and probable) to output values (shock probabilities) in one embodiment of a defuzzification process.

Step 42: Fuzzification process. This process performs the transformation of input values to a grade of membership for all linguistic terms to be used for the conditions. The input values are the clinical or hemodynamic parameter values which were normalized by their normal ranges in module 21. This step is illustrated in FIG. 5 and described in more detail below. One example of the fuzzification process for a heart rate of 95 bpm and a normalized range of 54-90 bpm is illustrated in FIG. 8, also described in more detail below.

Step 44: Fuzzy inference machine: This machine is the core process of the Fuzzy system. It transforms the grade of membership of linguistic terms which are used in the conditions of a set of Fuzzy rules to a grade of membership of linguistic terms such as improbable, possible, and probable which are used in the conclusions of a set of Fuzzy rules. Greater numbers of linguistic terms result in more precision (see examples below adding terms such as very improbable and very probable). A Fuzzy rule is a linguistic formulation of condition(s) resulting in one conclusion, e.g. IF (STR is low) OR (STR is normal) THEN (Hypovolemic Shock is probable), where STR=Systolic time ratio. Similar rules are used for the other input values for hemodynamic parameters, as described in more detail below.

Figure 6:
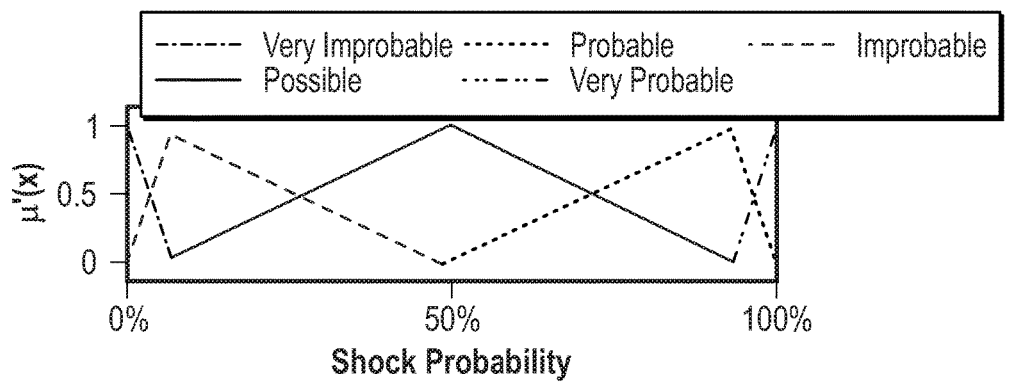
FIG. 6 illustrates another embodiment of a defuzzification process in which five linguistic conclusion terms (very improbable, improbable, possible, probable and very probable) are assigned to output values (shock probabilities)
Figure 7:
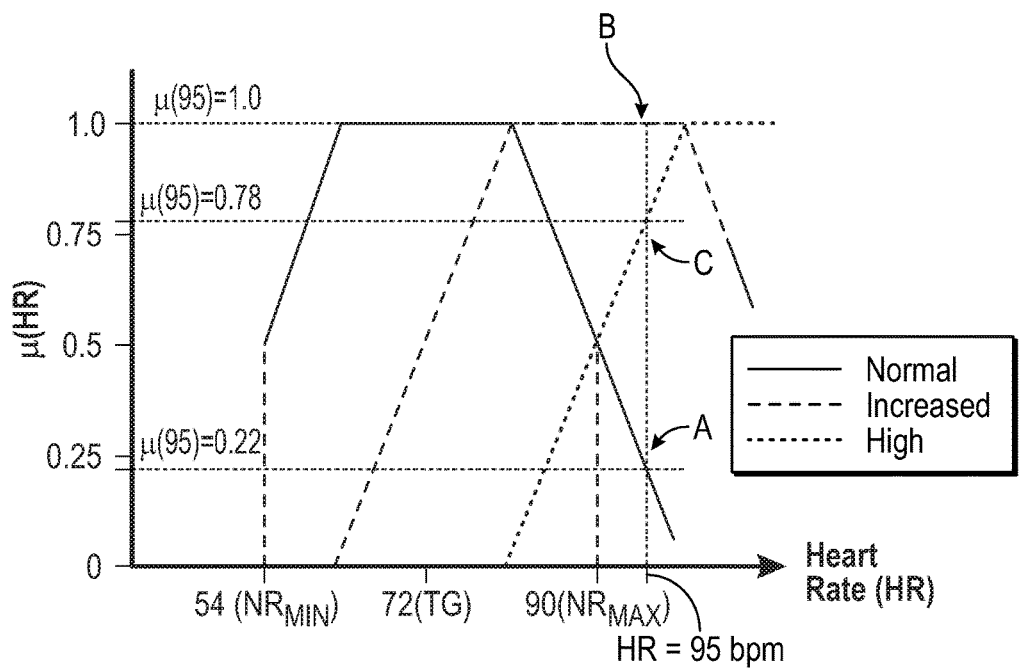
FIG. 7 illustrates the fuzzification of one example of a heart rate of 95 bpm with a normal range of 54 to 90 bpm.

Step 45: Defuzzification process: This process performs the transformation of the grade of membership for all linguistic terms to be used for the conclusions to output values. The output values in step 46 are the partial probabilities for each clinical parameter used in determination of probability of the different shock cases. FIGS. 6 and 7 illustrate embodiments of the defuzzification process, as described in more detail below.

Figure 4:
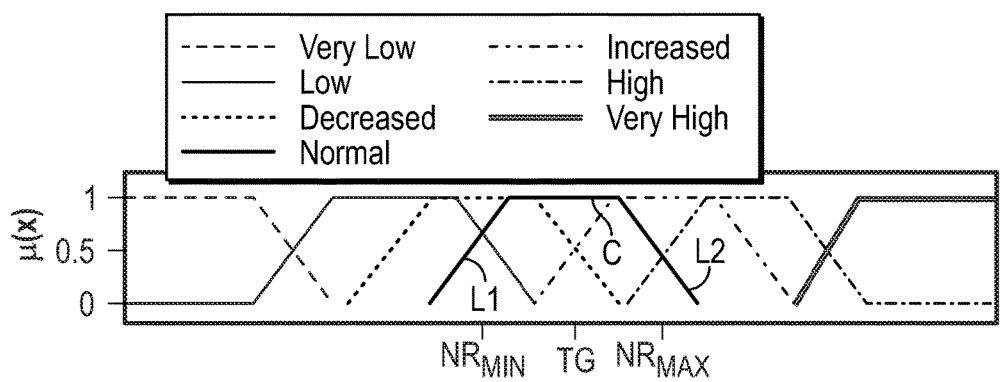
FIG. 4 illustrates assignment of normalized input parameter values to five linguistic terms corresponding to different shock probabilities for use in one embodiment of a fuzzification process.

FIGS. 4 to 9 illustrate fuzzification and defuzzification methods to transform an input value, for example a measured cardiac or other clinical parameter, into a grade of membership, for example "normal" or "high". FIG. 4 illustrates the assignment of linguistic terms normal, low or very low, and high or very high for fuzzification of a measured parameter, using normalized ranges for the respective parameters selected for use in the probability determination process (step 42 of FIG. 3). FIG. 5 illustrates a defuzzification process to transform the measured parameter into an output value or shock probability (steps 44 and 45). The terms in FIG. 4 are each outlined as shapes which resemble a tetragon, while the shapes for defuzzification in FIG. 5 resemble a triangle. Other embodiments may employ different shapes for fuzzification and defuzzification, for example part of a sinusoid or Gaussian distribution.

FIG. 4 illustrates fuzzification of a parameter where a normalized range of values for that parameter is from $NR_{MIN}$=normal range minimum to $NR_{MAX}$=normal range maximum, where TG=therapeutic goal or center of normal range and $\mu(x)$ is the probability. The black line defines a central portion C around TG which corresponds to a probability of 1, and lines L1, L2 extending from each end of the central portion at an angle from probability 1 to 0. In this embodiment, $NR_{MIN}$ and $NR_{MAX}$ correspond to the midpoint (membership of 0.5 to linguistic term normal) of lines L1, L2, respectively, but other locations of different probability may be chosen in other embodiments. The tetragon encloses an area corresponding to the term normal within these lines. Similar tetragon-shaped areas are defined in FIG. 5 for the linguistic terms decreased (dotted line centered on $NR_{MIN}$), low (gray line), very low (black dashed line) and increased (gray dashed line centered on $NR_{MAX}$), high (dot-dash line) and very high (double line). Only part of the tetragon shape is shown for the terms very low and very high.

FIG. 5 illustrates one example of part of step 44 (defuzzification process) where three linguistic conclusion terms (improbable, possible, and probable) are assigned to output values or shock probabilities with shapes outlining a triangle, where improbable=Dashed line, Possible=solid line, and Probable=dotted line. Note that the more linguistic terms are defined, the better the differentiation between shock probabilities. FIG. 7 illustrates an example of a defuzzification process where five linguistic conclusion terms (very improbable, improbable, possible, probable, and very probable) are assigned to the output values or shock probabilities from 0% to 100%. This process is carried out for each hemodynamic or clinical parameter, and each parameter contributes different probabilities for a shock case, each of which is weighted.

FIGS. 7 to 10 illustrate the fuzzy logic process or fuzzy system applied towards a shock decision system for one example of a hemodynamic parameter, in this case a heart rate (HR). Similar techniques are used for all other hemodynamic parameters used in a shock probability evaluation. FIG. 7 assumes a measured heart rate of 95 bpm and a normalized heart rate range of 54-90 bpm. Depending on the value obtained for the patient heart rate, the probability contribution towards a shock condition is determined by applying the rules for a shock condition. Other clinical parameters can be evaluated in a similar manner, as will be understood by one skilled in the art.

FIG. 7 illustrates the fuzzification of the clinical parameter value HR=95 bpm to the membership grades $\mu(HR)$ of three linguistic terms normal (solid line), increased (dashed line) and high (dotted line) which describe the clinical parameter value, similar to FIG. 5. The membership grades $\mu(HR)$ were derived from the previously determined normalized range for HR of 54 . . . 90 bpm with a center (TG, therapeutic goal) at 72 bpm. This range and therapeutic goal corresponds to an adult of average size. Since the measured HR is above this range, only the linguistic terms normal, increased, and high are used. In FIG. 8, the area bounded by the solid line indicates fuzzification for a normal heart rate, with a center at 72 bpm. The area bounded by the dashed line indicates fuzzification for an increased heart rate, and the area bounded by the dotted line indicates fuzzification for a high heart rate. Each area has an upper flat line corresponding to a membership of 1 with centers corresponding to the center of the range for normal, increased and high heart rate ranges, and left and right inclined lines extending upward at an angle from the x-axis to the left and right ends, respectively, of the upper flat line, with $NR_{MIN}$ and $NR_{MAX}$ located at the 0.5 probability point for the respective normal heart rate angled lines.

FIG. 8 is similar to FIG. 7 but shows implementation of two simple rules for probability of any type of shock condition (generic shock condition):

Rule 1: A 'normal' heart rate concludes that a shock is improbable.

Rule 2: A 'high' heart rate concludes that a shock is probable.

FIG. 8 illustrates the function of the Fuzzy inference machine implementing these two rules. Regarding the input parameter (HR), the rules above specify only 'normal' and 'high' conditions for HR. No rule is established for 'increased' HR and thus this is not considered in the figure.

Regarding the outcome, the above rules refer only to the linguistic terms 'improbable' and 'probable'. No rule specifies the condition 'possible'. In FIG. 7, the linguistic terms 'normal', 'increased' and 'high' are used to describe the HR value of 95 bpm (with a membership grade of 0.22, 1.0 and 0.78 respectively, illustrated by the horizontal lines), i.e. the membership μ(95, normal) for normal is 0.22, the probability or membership μ(95, increased) that the heart rate HR corresponds to the linguistic term increased is 1.0, and the membership μ(95, high) is 0.78, as determined by the intersection between the vertical HR line at 95 bpm with the "normal" line at A, the "increased" upper line at B, and the "high" line at C.

The embodiment of FIG. 8 establishes just two memberships, i.e., 'normal' and 'high'. In this embodiment (in which the normal and high memberships correspond to the normal and high memberships of FIG. 7), the membership value μ(95, normal) for 'normal' of a HR of 95 bpm is 0.22. The membership value μ(95, high) for 'high' of a HR of 95 bpm is 0.78. A higher measured heart rate leads to higher value μ(95, high) and a lower value for μ(95, normal).

FIG. 9 illustrates defuzzification of the fuzzified heart rate values for μ(95, high) and μ(95, normal) in FIG. 8. The embodiment of FIG. 9 illustrates the assignment of three linguistic terms to output values (shock probabilities). Because no rule is existent for the linguistic term 'possible', the triangle with its tip at 50% is not considered.

Figure 10:
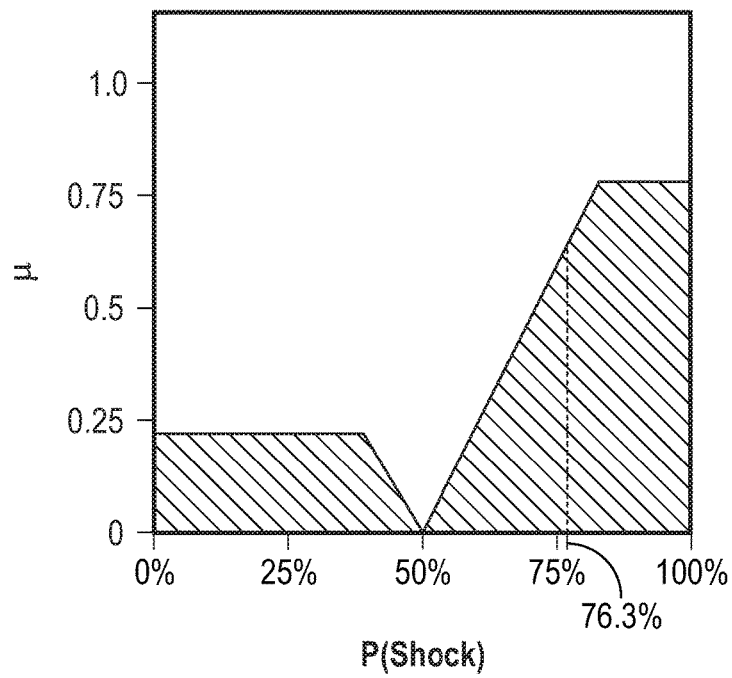
FIG. 10 is an expanded view of part of the shock probability graph of FIG. 9 illustrating the defuzzification of shock memberships to a probability.

The membership values μ(95, normal)=0.22 and μ(95, high)=0.78 as determined in the fuzzification process of FIG. 7 and shown in FIG. 8 limit the output values for the output 'improbable' and 'probable'. These limits plus the remaining limits established by the triangles representing 'improbable' and 'probable' (=two scaled membership functions) define an envelope curve and an area below it, as illustrated separately in FIG. 10. FIG. 10 is an extraction of part of the graph of FIG. 9 to illustrate one embodiment of the defuzzification of the linguistic terms which were activated by the fuzzy rule set into a shock probability based on the measured, normalized heart rate of 95 bpm.

Different methods can be used for assessing the area under the curve in FIG. 10 and translating it into the probability that a HR of 95 bpm is a symptom of generic shock based on the two simple rules mentioned above for generic shock being improbable or probable. In the illustrated embodiment the method COA (Center of Area) is employed to determine the center of the area under the (two) scaled membership functions. Using this method, a probability of 0.763 was determined for HR=95 bpm. Other methods which can be implemented are, but not limited to, COG (Center of Gravity) and the MeOM (Mean of Maximum).

The result is a partial shock probability, meaning that more clinical or hemodynamic parameters must be assessed and considered to determine a specific shock condition more reliably. It has to be noted that in the presence of dysrhythmia or abnormal heart rate, the decision system must be adapted accordingly or not applied at all.

In the system and method of FIGS. 1 to 3, one or more clinical parameters are considered and each selected parameter undergoes the process of fuzzification and defuzzification illustrated in FIGS. 4 to 9 in order to determine a generic or specific shock probability. A low mean arterial pressure (MAP) is another symptom of a shock condition. The partial shock probability of a specific MAP value can be determined by fuzzification and de-fuzzification in the same way as illustrated in FIGS. 7 to 10 for heart rate. This partial probability is weighted together with other selected partial probabilities in determining the shock probability, leading to a combined probability for a particular shock case. Heart rate (HR) and MAP probability alone may be used to determine the generic shock probability, but other combinations of parameters may be used in alternative embodiments for determining generic and specific shock type probability.

Figure 11:
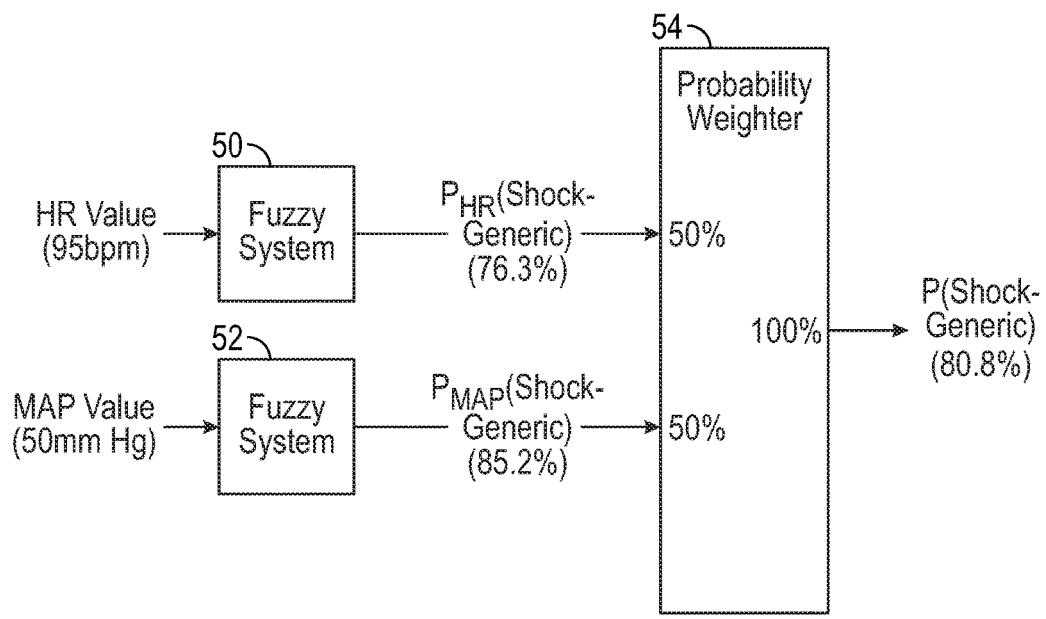
FIG. 11 illustrates one embodiment of weighting of two partial shock probabilities to a combined probability for a generic shock situation.

FIG. 11 illustrates an embodiment in which HR and MAP partial probabilities are used for determining generic shock (i.e., a shock condition without further differentiation whether it is of cardiogenic, hypovolemic, septic, or anaphylactic origin). In this embodiment, the probabilities of both parameters HR and MAP are weighted equally (50% each). In the illustrated example, a HR of 95 bpm and a MAP of 50 mmHg lead to a probability of 80.8% for a generic shock condition. Thus, in step 50 of FIG. 3, the fuzzification system generally illustrated in FIGS. 7 to 10 converts the heart rate of 95 bpm into a heart rate based, generic shock probability $P_{HR}$ (shock generic) of 76.3% or 0.763. The same system converts a MAP of 50 mm Hg to a MAP based, generic shock probability $P_{MAP}$ of 85.2%. A probability weighting step 54 then combines the two shock probabilities at weightings of 50% each to produce a probability or P(shock generic) of 0.808, i.e. $0.5 P_{HR} + 0.5 P_{MAP} = 80.8\%$. In other words, this is a probability that a shock condition exists, without any indication of the likely type of shock involved.

Figure 12:
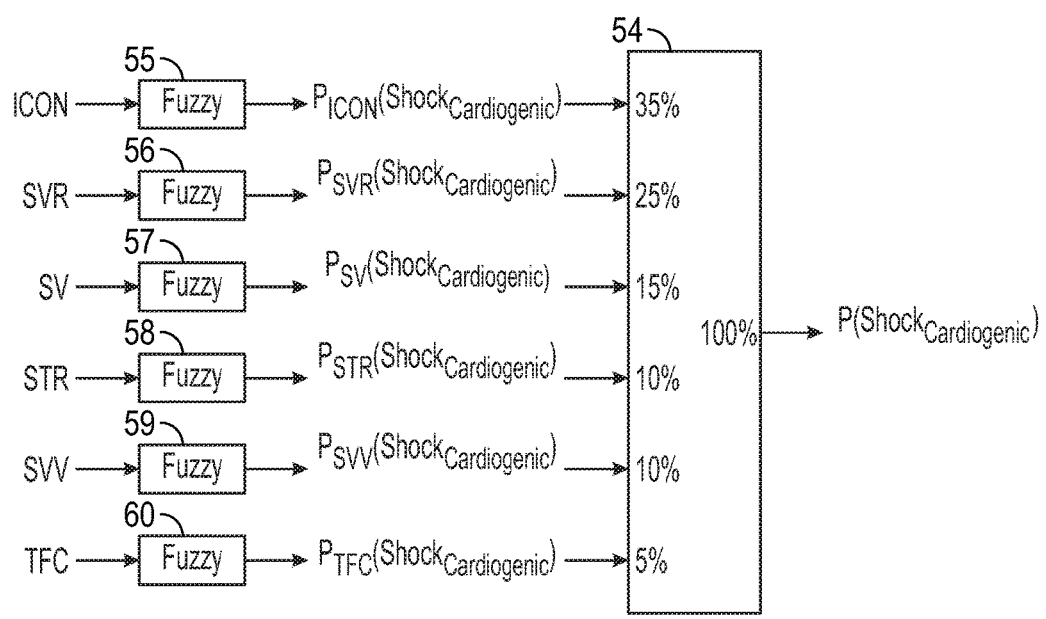
FIG. 12 illustrates one embodiment of weighting of six partial shock probabilities based on six hemodynamic parameters to a combined probability for cardiogenic shock.

FIG. 12 illustrates an embodiment for determining likelihood of a particular type of shock, in this example a cardiogenic shock condition where the probability of cardiogenic shock is based on normalized hemodynamic or other clinical/viral parameters. In this embodiment, the selected parameters are ICON (Index of Contractility), SVR (Systemic Vascular Resistance), SV (Stroke Volume), STR (Systolic Time Ratio), SVV (Stroke Volume Variation) and TFC (Thoracic Fluid Content), but different parameters or a greater or lesser number of parameters may be used in other embodiments. In this embodiment, the partial shock probability for cardiogenic shock based on each hemodynamic parameter is determined using the fuzzy system described above in steps 55 (ICON), 56 (SVR), 57 (SV), 58 (STR), 59 (SVV) and 60 (TFC). In the probability weighting step 54, each of the partial shock probabilities are assigned the following weights: $P_{ICON}=35\%$, $P_{SVR}=25\%$, $P_{SV}=15\%$, $P_{STR}=10\%$, $P_{SVV}=10\%$, and $P_{TFC}=5\%$. In other words, the contributions of the six hemodynamic parameters vary between 5% and 35%. This results in an overall cardiogenic shock probability P (shock cardiogenic), where six clinical and hemodynamic parameters contribute with different weights to a cardiogenic shock condition. The weighting reflects the importance of these parameters in indicating shock. Parameters such as TFC (here: weighting=5%) may be eliminated from the process at the expense of reliability, or more parameters may be added in order to increase reliability.

With little or no adaption, the parameter SVV can be exchanged with PVI™ (Pleth Variability Index as offered in devices from Masimo™, Irvine, Va., USA), FTc (or corrected flow time, which is flow time normalized for heart rate), or PPV (Pulse Pressure Variation), as described by Michard et al. "Pulse pressure variation: beyond the fluid management of patients with shock" (see http://www.ccforum.com/content/11/3/131), which is hereby incorporated by reference. In some embodiments, both parameters FTc and SVV may be included.

Figure 13:
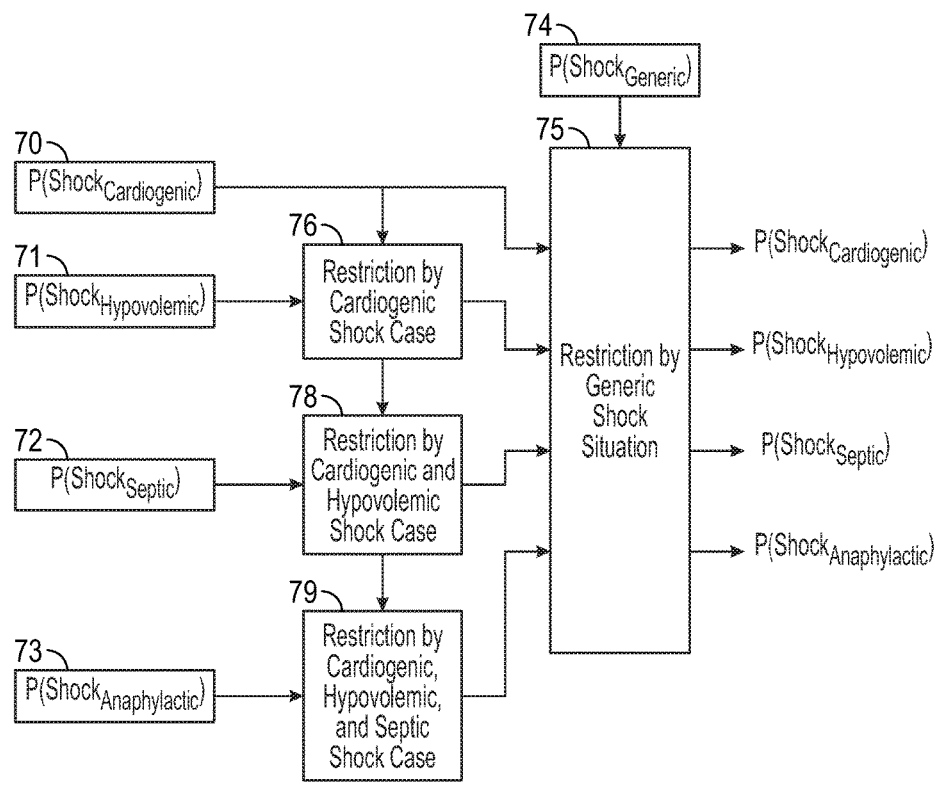
FIG. 13 illustrates one embodiment of restriction of different shock type probabilities by other shock type probabilities and by the evaluation of the generic shock probability, following the approach of clinical decision making.

FIG. 13 illustrates one embodiment of a method for determining the probability of the four shock cases cardiogenic, hypovolemic, septic and anaphylactic shock. In this method, initial probabilities for the four shock types (cardiogenic, hypovolemic, septic, and anaphylactic) are determined in steps 70, 71, 72 and 73, respectively. These probabilities may be determined using fuzzy logic as illustrated in FIGS. 6 to 10 and 12 for a cardiogenic shock condition. The probability of a generic shock condition (shock of any type) is determined in step 74, as illustrated in FIG. 10. In step or module 75, each shock probability is restricted by the generic shock probability. In other words, the determined shock probability of the last step is modified for all these shock cases if the heart rate and the mean arterial blood pressure (see FIG. 12) indicate that a shock situation is possible or probable. Furthermore a specific shock probability may restrict the shock probability of another shock type if the first shock type is probable, as illustrated in steps 76, 78 and 79 and described in more detail below. This reflects the clinical decision process in which the exclusion of certain hemodynamic conditions leads to the final diagnosis. In one embodiment, the cardiogenic shock probability determined in step 70 is restricted based on the generic shock probability (step 75). If a cardiogenic shock is not probable (and can be excluded), the system gives consideration to the hypovolemic shock case (step 76), and after exclusion also to the allergy shock cases, with septic shock considered first (step 78) and if that type of shock is excluded, anaphylactic shock is considered. Each of these shock probabilities is also modified by the generic shock probability in step 75.

The decision system of FIG. 13 follows the clinical approach. Note that the number of clinical or hemodynamic parameters and number of rules may be more or less depending on the availability of a parameters and intended complexity of the decision system.

The following lists one embodiment of rules for determination of the probabilities for generic shock (GS), cardiogenic shock (CS), hypovolemic shock (HS), septic shock (SS) and anaphylactic shock (AS), and describes the evaluation in one exemplary embodiment in more detail. The rules define which conditions must be met in linguistic terms.

Restrictions are established by an additional set of local rules (not to be confused with fuzzy logic rules):
1. Only when the conditions for a generic shock are met, specific shock types are further considered and differentiated. That said the probability of a specific shock type is governed by the probability of a generic shock.
2. The probability of a cardiogenic shock restricts all other shock types because the rules and parameters and corresponding terms do not 'overlap' so much with the other shock types.
3. The probabilities of cardiogenic and hypovolemic shock (whichever is highest) restrict the probabilities of septic shock.
4. The probabilities of cardiogenic, hypovolemic and septic shock (whichever has the highest probability) restrict the probabilities of anaphylactic shock.

Other embodiments can be constructed which use more or less specificity regarding rules, parameters, and terms. Furthermore, there are multiple ways to implement a Fuzzification and Defuzzification process. Weighting of each parameter contributing to a shock probability or membership ($\mu$ or $\mu'$) may be adjusted in the presence of more clinical data.

In this embodiment, the generic shock decision is based on heart rate (HR) and mean arterial blood pressure (MAP) using rules listed in Table 1 and described in more detail below, but other parameters and rules may be used in alternative embodiments.

TABLE 1

Rules for Generic Shock

| Relevance/Weight | Parameter | Rule # | Condition of Value | Evaluation (Shock) |
|---|---|---|---|---|
| 50% | HR | S 1 a) | High or very high | Probable |
|  |  | S 1 b) | Normal or lower | Improbable |
| 50% | MAP | S 2 a) | Low or very low | Probable |
|  |  | S 2 b) | Normal or higher | Improbable |

1. Rules with parameter HR (50% weight)
RULE 1: IF (HeartRate IS high) OR (HeartRate IS very_high) THEN GenericShock_HR IS probable;
RULE 2: IF (HeartRate IS normal) OR (HeartRate IS low) OR (HeartRate IS very_low) THEN GenericShock_HR IS improbable;
2. Rules with parameter MAP (50% weight)
RULE 3: IF (MeanArterialBloodPressure IS low) OR (MeanArterialBloodPressure IS very_low) THEN GenericShock_MAP IS probable;
RULE 4: IF (MeanArterialBloodPressure IS normal) OR (MeanArterialBloodPressure IS high) OR (MeanArterialBloodPressure IS very_high) THEN GenericShock_MAP IS improbable.

In the embodiment illustrated in FIG. 12, the rules for determining probability of cardiogenic shock are based on six clinical and hemodynamic parameters, specifically ICON (Index of contractility); SVR (Systemic vascular resistance); SV (Stroke volume); STR (Systolic time ratio); SVV (Stroke volume variation) and TFC (Thoracic fluid content). These parameters are weighted differently leading to different influences on the resulted probability, with SVR and ICON having the highest weights as predictors for cardiogenic shock. The probability for this shock case additionally depends on the probability for a shock situation in general. Table 2 illustrates one example of rules and weightings for evaluating cardiogenic shock probability using the above parameters. The parameters and weightings used to evaluate probability or cardiogenic shock may be modified in other embodiments.

TABLE 2

Rules for Cardiogenic Shock

| Relevance/Weight | Parameter | Rule # | Condition of Value | Evaluation (Cardiogenic Shock) |
|---|---|---|---|---|
| 35% | ICON | CS 1 a) | very low | probable |
|  |  | CS 1 b) | low | possible |
|  |  | CS 1 c) | normal or higher | improbable |
| 25% | SVR | CS 2 a) | increased | probable |
|  |  | CS 2 b) | not increased | improbable |
| 15% | SV | CS 3 a) | low or very low | probable |
|  |  | CS 3 b) | normal or higher | improbable |
| 10% | STR | CS 4 a) | high | probable |
|  |  | CS 4 b) | very high | possible |
|  |  | CS 4 c) | normal or lower | improbable |
| 10% | SVV | CS 5 a) | increased | probable |
|  |  | CS 5 b) | not increased | improbable |
| 5% | TFC | CS 6 a) | low or very low | probable |
|  |  | CS 6 b) | normal or higher | improbable |

The weightings used in Table 2 may be modified in other embodiments, and additional or different parameters may be included in alternative embodiments, for example heart rate (HR), mean arterial blood pressure (MAP), and cardiac output (CO) with appropriate weightings adding up to 100%. In one embodiment, rules CS 5a) and CS5b) may be replaced with FTc decreased=Probable and SVV lowered=improbable, respectively.

In one embodiment, the rules for hypovolemic shock are based on six clinical and hemodynamic parameters. As with cardiogenic shock evaluation, these parameters are weighted differently leading to different influence on the resulted probability, as illustrated in Table 3. The same parameters are used in both the cardiogenic and hypovolemic shock evaluation in this embodiment, but SVV has a higher weight and ICON has a lower weight in the hypovolemic shock calculation. The probability for this shock case additionally depends on the probability for a shock situation in general. Finally the probability for this shock case is reduced based on the probability of the cardiogenic shock. Again, the parameters and weightings used to evaluate probability of hypovolemic shock may be modified in other embodiments.

TABLE 3

Rules for Hypovolemic Shock

| Relevance/ Weight | Parameter | Rule # | Condition of Value | Evaluation (Hypovolemic Shock) |
|---|---|---|---|---|
| 30% | SVV | HS 1 a) | very high | probable |
|  |  | HS 1 b) | high | possible |
|  |  | HS 1 c) | normal or lower | improbable |
| 20% | ICON | HS 2 a) | normal or higher | probable |
|  |  | HS 2 b) | low or very low | improbable |
| 20% | SVR | HS 3 a) | increased | probable |
|  |  | HS 3 b) | not increased | improbable |
| 10% | SV | HS 4 a) | decreased | probable |
|  |  | HS 4 b) | not decreased | improbable |
| 10% | STR | HS 5 a) | low or normal | probable |
|  |  | HS 5 b) | very low | possible |
|  |  | HS 5 c) | high or very high | improbable |
| 10% | TFC | HS 6 q) | very low | probable |
|  |  | HS 6 b) | low | possible |
|  |  | HS 6 c) | normal or higher | improbable |

In another embodiment, the above rules for parameter SVV are changed to consider FTc instead of SVV, as follows: Rule HS 1 a) FTc very low=probable, Rule HS 1 b) FTc low=possible.

In one embodiment, the rules for septic shock are based on five clinical and hemodynamic parameters, specifically SVR, CO (cardiac output), ICON, SVV and TFC, with SVR and CO having the highest weights. These parameters are weighted differently, as illustrated in Table 4 below, leading to different influence on the resultant probability. The probability for this shock case additionally depends on the probability for a shock situation in general. Finally the probability for this shock case also depends on the probability of the cardiogenic and hypovolemic shock. If either a cardiogenic shock or a hypovolemic shock is probable, the probability for septic shock is restricted. The parameters and weightings used to evaluate probability of septic shock may be modified in other embodiments.

TABLE 4

Rules for Septic Shock

| Relevance/ Weight | Parameter | Rule # | Condition of Value | Evaluation (Septic Shock) |
|---|---|---|---|---|
| 35% | SVR | SS 1 a) | very low | probable |
|  |  | SS 1 b) | low, normal or higher | improbable |

TABLE 4-continued

Rules for Septic Shock

| Relevance/ Weight | Parameter | Rule # | Condition of Value | Evaluation (Septic Shock) |
|---|---|---|---|---|
| 35% | CO | SS 2 a) | very high | probable |
|  |  | SS 2 b) | high | possible |
|  |  | SS 2 c) | normal or lower | improbable |
| 15% | ICON | SS 3 a) | high or very high | probable |
|  |  | SS 3 b) | normal or lower | improbable |
| 5% | SVV | SS 4 a) | increased | probable |
|  |  | SS 4 b) | not increased | improbable |
| 10% | TFC | SS 5 a) | increased | probable |
|  |  | SS 5 b) | not increased | improbable |

In another embodiment, the above rules for parameter SVV may be changed to consider FTc in addition to SVV, as follows: Rule SS 4 a) FTc decreased=probable; Rule SS 5 b) SSV lowered=improbable.

In this embodiment the rules for anaphylactic shock are based on three clinical and hemodynamic parameters, specifically SVR, CO and TFC, as illustrated in Table 5 below. The parameters SVR and CO have the same weight and thus the same influence on the resultant probability. The probability for this shock case additionally depends on the probability for a shock situation in general. Finally the probability for this shock case depends on the probability of the cardiogenic, hypovolemic and septic shock. If one of those three shock cases is probable, the probability for an anaphylactic shock is restricted. The parameters and weightings used to evaluate probability of anaphylactic shock may be modified in other embodiments. For example, in one alternative, TFC is not considered in determining the probability of anaphylactic shock, and SVR and CO only are considered, with a 50% weight for each of these parameters.

TABLE 5

Rules for Anaphylactic Shock

| Relevance/ Weight | Parameter | Rule # | Condition of Value | Evaluation (Anaphylactic Shock) |
|---|---|---|---|---|
| 45% | SVR | AS 1 a) | Low | probable |
|  |  | AS 1 b) | very low, normal or higher | improbable |
| 45% | CO | AS 2 a) | Increased | probable |
|  |  | AS 2 b) | not increased | Improbable |
| 10% | TFC | AS 3 a) | Increased | probable |
|  |  | AS 3 b) | not increased | improbable |

The previously described embodiments refer to sets of clinical or hemodynamic parameters which are well suited for identification and differentiation of shock. Other clinical and hemodynamic parameters, or a combination of them, may serve as a substitute for one or more of the aforementioned parameters. The weights applied in the tables above and to each partial probability shown in FIG. 12 serve as an example and are approximate and may be adjusted upon more collected clinical evidence or because of substitution by other parameters.

As described above, once the initial shock probability for each shock type as well as generic shock are determine by the fuzzy logic method or by other methods such as neural network or algorithms, each partial shock probability may be adjusted based on the generic shock probability and may also be reduced or restricted by probability of another type of shock. Each probability is a number between 0 and 1. As noted above, the two methods of restricting the shock type probabilities determined by Fuzzy Logic for shock differentiation are generic shock probability and probability of a different type of shock. These two methods are described in more detail below.

1. Generic Shock Probability (Elevated HR, Low BP)

The membership to the value 'improbable' is used for reduction. The value is between 0 and 1. Accordingly, for all shock types the reduction can be stated as:

$$P^*(\text{shock type}) = P(\text{shock type}) * (1 - M(\text{generic shock condition}, \text{'improbable'}))  \quad \text{Equation 1,}$$

Where P(shock type)=Probability of shock type (for instance, hypovolemic) as initially determined by Fuzzy Logic.
P*(shock type): restricted/reduced probability of shock type based on generic shock probability.
M (generic shock condition, 'improbable'): membership value or probability for the generic shock condition (i.e., elevated HR, low BP) to have the value 'improbable'.

In the example of FIG. 11, P (generic shock condition)= 0.808, which corresponds to a generic shock probability of probable. Thus, other shock probabilities in this case are not reduced based on generic shock condition, since M (generic shock condition, improbable)=0.

2. Restriction by Probability of Another Shock Type

The rules for further adjustment of probabilities of different shock types in one embodiment are:
1. 'Cardiogenic' is not restricted.
2. 'Hypovolemic' is restricted by 'Cardiogenic'.
3. 'Septic' is restricted by either 'Cardiogenic' or 'Hypovolemic' (whichever has the higher probability).
4. 'Anaphylactic' is restricted by 'Cardiogenic' or 'Hypovolemic or Septic' (whichever has the higher probability).

Accordingly, the additional reduction/restriction can be stated as:

$$P'(\text{shock type}) = P^*(\text{shock type}) * (1 - \max M(\text{other shock type}, \text{'probable'})) \quad \text{Equation 2}$$

P*(shock type): restricted probability of shock type due to 'generic shock condition'
P'(shock type): restricted probability of shock type due to other shock type probabilities.
M(other shock type, 'probable'): membership value for another shock case to have the value 'probable'. Of all shock types, the maximum M is considered.

Some examples of patient evaluations for scenarios involving cardiogenic, hypovolemic, septic and anaphylactic shock conditions using the embodiments of an automated system and method for evaluating patients for shock as described above are illustrated in Tables 7 to 10 below. These tables illustrate evaluations of various shock probabilities based patient data and on the rules described above. The first three columns of show the parameters used within this particular embodiment, the normal range (defined by therapeutic goals), and the parameter value measured off or obtained from a subject or record, respectively. The fourth column shows the memberships ($\mu$) of each parameter value and each term contributing to the decision process which are obtained from fuzzification diagrams. The fifth column shows the results, i.e., the probability of each parameter contributing to either generic shock or a specific shock type. If this probability is applied to a defuzzification diagram, the membership ($\mu'$) for each parameter for each term can be read. Note that these memberships are of importance when restrictions come into play and are calculated.

The (unrestricted) probability of generic shock and any shock type is determined by the product of each parameter's probability and weight (see result below each table). Similarly, based on the membership ($\mu$) of each parameter obtained in the Defuzzification process and the weight, the memberships of the shock type to each term ('improbable', 'possible', probable') are obtained (again, important for restriction).

The generic shock probability calculation for the example HR and MAP values in FIG. 11 is shown in Table 6 below.

TABLE 6

Generic shock probability calculation

| | | | | Evaluation "Generic Shock Condition" | |
|---|---|---|---|---|---|
| Param. | Normal Range | Value | Membership $\mu$(Input-Value, Term) | Probability $P_{Param}(\text{shock}_{generic})$ and Membership $\mu'(P, \text{Term})$ | Weight w |
| HR | 54-90 | 95 | $\mu$(95, "very low") = 0<br>$\mu$(95, "low") = 0<br>$\mu$(95, "decreased") = 0<br>$\mu$(95, "normal") = 0<br>$\mu$(95, "increased") = 0.944<br>$\mu$(95, "high") = 1<br>$\mu$(95, "very high") = 0 | $P_{HR}(\text{shock}_{generic})$ = 76.3%<br>$\mu'$(P, "improbable") = 0<br>$\mu'$(P, "possible") = 0.474<br>$\mu'$(P, "probable") = 0.526 | 0.5 |
| MAP | 80-100 | 50 | $\mu$(50, "very low") = 1<br>$\mu$(50, "low") = 0<br>$\mu$(50, "decreased") = 0<br>$\mu$(50, "normal") = 0<br>$\mu$(50, "increased") = 0<br>$\mu$(50, "high") = 0<br>$\mu$(50, "very high") = 0 | $P_{MAP}(\text{shock}_{generic})$ = 85.2%<br>$\mu'$(P, "improbable") = 0<br>$\mu'$(P, "possible") = 0.296<br>$\mu'$(P, "probable") = 0.704 | 0.5 |

This results in the following probabilities:
Overall Shock Probability: $P(\text{shock}_{generic})$=80.8%
Memberships of Probability: $\mu'(P_{GS}, \text{"improbable"})$=0
$\mu'(P_{GS}, \text{"possible"})$=0.385
$\mu'(P_{GS}, \text{"probable"})$=0.615

Table 7 below is an example of a patient with a high likelihood of cardiogenic shock. The "Normal Range" for each parameter is based on a therapeutic goal or average normal level for that parameter which is normalized based on patient parameters, as described above. The range is determined using a selected percentage around the normalized value, e.g. plus or minus a selected percentage in the range from around 10 to 25%. The value is the current measured value of each parameter. The rules for determining cardiogenic shock probability in this embodiment (as noted in Table 3 above) are:

Rules for Parameter ICON (35% Weight)
RULE 1: IF IndexOfContractility IS very_low THEN CardiogenicShock_ICON IS probable;
RULE 2: IF IndexOfContractility IS low THEN CardiogenicShock_ICON IS possible;
RULE 3: IF (IndexOfContractility IS normal) OR (IndexOfContractility IS high) OR (IndexOfContractility IS very_high) THEN CardiogenicShock_ICON IS improbable;
Rules for Parameter SVR (25% Weight)
RULE 4: IF SystemicVascularResistance IS increased THEN CardiogenicShock_SVR IS probable;
RULE 5: IF NOT (SystemicVascularResistance IS increased) THEN CardiogenicShock_SVR IS improbable;
Rules for Parameter SV (15% Weight)
RULE 6: IF (StrokeVolume IS low) OR (StrokeVolume IS very_low) THEN CardiogenicShock_SV IS probable;
RULE 7: IF (StrokeVolume IS normal) OR (StrokeVolume IS high) OR (StrokeVolume IS very_high) THEN CardiogenicShock_SV IS improbable;
Rules for Parameter STR (10% Weight)
RULE 8: IF SystolicTimeRatio IS high THEN CardiogenicShock_STR IS probable;
RULE 9: IF SystolicTimeRatio IS very_high THEN CardiogenicShock_STR IS possible;
RULE 10: IF (SystolicTimeRatio IS normal) OR (SystolicTimeRatio IS low) OR (SystolicTimeRatio IS very_low) THEN CardiogenicShock_STR IS improbable;
Rules for Parameter SVV (10% Weight)
RULE 11: IF StrokeVolumeVariation IS increased THEN CardiogenicShock_SVV IS probable;
RULE 12: IF NOT (StrokeVolumeVariation IS increased) THEN CardiogenicShock_SVV IS improbable;
Rules for Parameter TFC (5% Weight)
RULE 13: IF (ThoracicFluidContent IS low) OR (ThoracicFluidContent IS very_low) THEN CardiogenicShock_TFC IS probable;
RULE 14: IF (ThoracicFluidContent IS normal) OR (ThoracicFluidContent IS high) OR (ThoracicFluidContent IS very_high) THEN CardiogenicShock_TFC IS improbable.

TABLE 7

Cardiogenic shock probability calculation

| Param. | Normal Range | Value | Membership $\mu$(Value, Term) | Evaluation "Cardiogenic Shock" Probability $P_{Param}(shock_{cardiogenic})$ And Membership $\mu'(P, Term)$ | Weight w |
|---|---|---|---|---|---|
| ICON | 38-62 | 20 | $\mu$(20, "very low") = 1<br>$\mu$(20, "low") = 0<br>$\mu$(20, "decreased") = 0<br>$\mu$(20, "normal") = 0<br>$\mu$(20, "increased") = 0<br>$\mu$(20, "high") = 0<br>$\mu$(20, "very high") = 0 | $P_{ICON}(shock_{cardiogenic})$ = 85.2%<br>$\mu'$(P, "improbable") = 0<br>$\mu'$(P, "possible") = 0.296<br>$\mu'$(P, "probable") = 0.704 | 0.35 |
| SVR | 735-1225 | 1300 | $\mu$(1300, "very low") = 0<br>$\mu$(1300, "low") = 0<br>$\mu$(1300, "decreased") = 0<br>$\mu$(1300, "normal") = 0.194<br>$\mu$(1300, "increased") = 1<br>$\mu$(1300, "high") = 0.806<br>$\mu$(1300, "very high") = 0 | $P_{SVR}(shock_{cardiogenic})$ = 85.2%<br>$\mu'$(P, "improbable") = 0<br>$\mu'$(P, "possible") = 0.296<br>$\mu'$(P, "probable") = 0.704 | 0.25 |
| SV | 77-128 | 50 | $\mu$(50, "very low") = 0<br>$\mu$(50, "low") = 1<br>$\mu$(50, "decreased") = 0.441<br>$\mu$(50, "normal") = 0<br>$\mu$(50, "increased") = 0<br>$\mu$(50, "high") = 0<br>$\mu$(50, "very high") = 0 | $P_{SV}(shock_{cardiogenic})$ = 85.2%<br>$\mu'$(P, "improbable") = 0<br>$\mu'$(P, "possible") = 0.296<br>$\mu'$(P, "probable") = 0.704 | 0.15 |
| STR | 0.3-0.5 | 0.6 | $\mu$(0.6, "very low") = 0<br>$\mu$(0.6, "low") = 0<br>$\mu$(0.6, "decreased") = 0<br>$\mu$(0.6, "normal") = 0<br>$\mu$(0.6, "increased") = 0.5<br>$\mu$(0.6, "high") = 1<br>$\mu$(0.6, "very high") = 0 | $P_{STR}(shock_{cardiogenic})$ = 85.2%<br>$\mu'$(P, "improbable") = 0<br>$\mu'$(P, "possible") = 0.296<br>$\mu'$(P, "probable") = 0.704 | 0.10 |
| SVV | 5-15 | 14 | $\mu$(14, "very low") = 0<br>$\mu$(14, "low") = 0<br>$\mu$(14, "decreased") = 0<br>$\mu$(14, "normal") = 0.7<br>$\mu$(14, "increased") = 1<br>$\mu$(14, "high") = 0.30<br>$\mu$(14, "very high") = 0 | $P_{SVV}(shock_{cardiogenic})$ = 85.2%<br>$\mu'$(P, "improbable") = 0<br>$\mu'$(P, "possible") = 0.296<br>$\mu'$(P, "probable") = 0.704 | 0.10 |
| TFC | 80-100 | 50 | $\mu$(50, "very low") = 1<br>$\mu$(50, "low") = 0<br>$\mu$(50, "decreased") = 0<br>$\mu$(50, "normal") = 0<br>$\mu$(50, "increased") = 0<br>$\mu$(50, "high") = 0<br>$\mu$(50, "very high") = 0 | $P_{TFC}(shock_{cardiogenic})$ = 85.2%<br>$\mu'$(P, "improbable") = 0<br>$\mu'$(P, "possible") = 0.296<br>$\mu'$(P, "probable") = 0.704 | 0.05 |

Probability results from Tables 6 and 7:
  Overall Shock Probability: $P(shock_{cardiogenic})$=85.2%
  Memberships of Probability: $\mu'(P_{CS}, \text{"improbable"})$=0
    $\mu'(P_{CS}, \text{"possible"})$=0.296
    $\mu'(P_{CS}, \text{"probable"})$=0.704
  Restriction factor for generic shock condition: 1−$\mu(P_{GS}, \text{"improbable"})$=1−0=1
  Restricted Cardiogenic Shock Probability: $P'(shock_{cardiogenic})$=85.2%

In Table 7, some or all of the rules for SVV used in the calculation may be replaced by rules for FTc, as noted above in connection with Table 2.

The heart rate and MAP parameters in Table 6 indicate a high probability of some type of shock condition, so the cardiogenic shock probability is not restricted by any low or improbable generic shock probability. In other words, the cardiogenic shock probability as calculated using the parameters ICON, SV, STR, SVV, SVR and TFC according to the rules above is 85.2% and is not restricted by any other shock probability.

Table 8 below is one example of a test case for processing a hypovolemic shock probability with restrictions based on the generic shock probability and cardiogenic shock probabilities as evaluated above. This evaluation uses the following rules, as outlined in Table 3 above:

Rules for Parameter ICON (20% Weight)
RULE 1: IF (IndexOfContractility IS normal) OR (IndexOfContractility IS high) OR (IndexOfContractility IS very_high) THEN HypovolemicShock_ICON IS probable;
RULE 2: IF (IndexOfContractility IS low) OR (IndexOfContractility IS very_low) THEN HypovolemicShock_ICON IS improbable;
Rules for Parameter SVR (20% Weight)
RULE 3: IF SystemicVascularResistance IS increased THEN HypovolemicShock_SVR IS probable;
RULE 4: IF NOT (SystemicVascularResistance IS increased) THEN HypovolemicShock_SVR IS improbable;
Rules for Parameter SV (10% Weight)
RULE 5: IF StrokeVolume IS decreased THEN HypovolemicShock_SV IS probable;
RULE 6: IF NOT (StrokeVolume IS decreased) THEN HypovolemicShock_SV IS improbable;
Rules with Parameter STR (10% Weight)
RULE 7: IF (SystolicTimeRatio IS low) OR (SystolicTimeRatio IS normal) THEN HypovolemicShock_STR IS probable;
RULE 8: IF SystolicTimeRatio IS very_low THEN HypovolemicShock_STR IS possible;
RULE 9: IF (SystolicTimeRatio IS high) OR (SystolicTimeRatio IS very_high) THEN HypovolemicShock_STR IS improbable;
Rules for parameter SVV (30% weight) (Note that these rules may be replaced by rules for parameter FTc in an alternative embodiment, as described above in connection with Table 3).
RULE 10: IF StrokeVolumeVariation IS very_high THEN HypovolemicShock_SVV IS probable;
RULE 11: IF StrokeVolumeVariation IS high THEN HypovolemicShock_SVV IS possible;
RULE 12: IF (StrokeVolumeVariation IS normal) OR (StrokeVolumeVariation IS low) OR (StrokeVolumeVariation IS very_low) THEN HypovolemicShock_SVV IS improbable;
Rules for Parameter TFC (10% Weight)
RULE 13: IF ThoracicFluidContent IS very_low THEN HypovolemicShock_TFC IS probable;
RULE 14: IF ThoracicFluidContent IS low THEN HypovolemicShock_TFC IS possible;
RULE 15: IF (ThoracicFluidContent IS normal) OR (ThoracicFluidContent IS high) OR (ThoracicFluidContent IS very_high) THEN HypovolemicShock_TFC IS improbable.

TABLE 8

Hypovolemic Shock Evaluation

| Param. | Normal Range | Value | Membership $\mu$(Value, Term) | Evaluation "Hypovolemic Shock" Probability $P_{Param}(shock_{hypovolemic})$ And Membership $\mu'$(P, Term) | Weight w |
|---|---|---|---|---|---|
| ICON | 38-62 | 20 | $\mu$(20, "very low") = 1<br>$\mu$(20, "low") = 0<br>$\mu$(20, "decreased") = 0<br>$\mu$(20, "normal") = 0<br>$\mu$(20, "increased") = 0<br>$\mu$(20, "high") = 0<br>$\mu$(20, "very high") = 0 | $P_{ICON}(shock_{hypovolemic})$ = 14.7%<br>$\mu'$(P, "improbable") = 0.706<br>$\mu'$(P, "possible") = 0.294<br>$\mu'$(P, "probable") = 0 | 0.20 |
| SVR | 735-1225 | 1300 | $\mu$(1300, "very low") = 0<br>$\mu$(1300, "low") = 0<br>$\mu$(1300, "decreased") = 0<br>$\mu$(1300, "normal") = 0.194<br>$\mu$(1300, "increased") = 1<br>$\mu$(1300, "high") = 0.806<br>$\mu$(1300, "very high") = 0 | $P_{SVR}(shock_{hypovolemic})$ = 85.2%<br>$\mu'$(P, "improbable") = 0<br>$\mu'$(P, "possible") = 0.296<br>$\mu'$(P, "probable") = 0.704 | 0.20 |
| SV | 77-128 | 50 | $\mu$(50, "very low") = 0<br>$\mu$(50, "low") = 1<br>$\mu$(50, "decreased") = 0.441<br>$\mu$(50, "normal") = 0<br>$\mu$(50, "increased") = 0<br>$\mu$(50, "high") = 0<br>$\mu$(50, "very high") = 0 | $P_{SV}(shock_{hypovolemic})$ = 37.8%<br>$\mu'$(P, "improbable") = 0.244<br>$\mu'$(P, "possible") = 0.756<br>$\mu'$(P, "probable") = 0 | 0.10 |
| STR | 0.3-0.5 | 0.6 | $\mu$(0.6, "very low") = 0<br>$\mu$(0.6, "low") = 0<br>$\mu$(0.6, "decreased") = 0<br>$\mu$(0.6, "normal") = 0<br>$\mu$(0.6, "increased") = 0.5<br>$\mu$(0.6, "high") = 1<br>$\mu$(0.6, "very high") = 0 | $P_{STR}(shock_{hypovolemic})$ = 14.7%<br>$\mu'$(P, "improbable") = 0.706<br>$\mu'$(P, "possible") = 0.294<br>$\mu'$(P, "probable") = 0 | 0.10 |

TABLE 8-continued

Hypovolemic Shock Evaluation

| Param. | Normal Range | Value | Membership µ(Value, Term) | Evaluation "Hypovolemic Shock" Probability $P_{Param}(shock_{hypovolemic})$ And Membership µ'(P, Term) | Weight w |
|---|---|---|---|---|---|
| SVV | 5-15 | 14 | µ(14, "very low") = 0<br>µ(14, "low") = 0<br>µ(14, "decreased") = 0<br>µ(14, "normal") = 0.7<br>µ(14, "increased") = 1<br>µ(14, "high") = 0.30<br>µ(14, "very high") = 0 | $P_{SVV}(shock_{hypovolemic})$ = 30.4%<br>µ'(P, "improbable") = 0.392<br>µ'(P, "possible") = 0.608<br>µ'(P, "probable") = 0 | 0.30 |
| TFC | 80-100 | 50 | µ(50, "very low") = 1<br>µ(50, "low") = 0<br>µ(50, "decreased") = 0<br>µ(50, "normal") = 0<br>µ(50, "increased") = 0<br>µ(50, "high") = 0<br>µ(50, "very high") = 0 | $P_{TFC}(shock_{hypovolemic})$ = 50.0%<br>µ'(P, "improbable") = 0<br>µ'(P, "possible") = 1<br>µ'(P, "probable") = 0 | 0.10 |

Probability results using Tables 6 to 8:
Overall Shock Probability: $P(shock_{hypovolemic})$=39.4%
Memberships of Probability: µ'($P_{HS}$, "improbable")= 0.212
µ'($P_{HS}$, "possible")=0.788
µ'($P_{HS}$, "probable")=0
Restriction factor for generic shock condition: 1−µ'($P_{GS}$, "improbable")=1−0=1
Restriction factor by other shock cases (CS): 1−µ'($P_{CS}$, "probable")=1−0.704=0.296
Restricted Hypovolemic Shock Probability: P'($shock_{hypovolemic}$)=39.5×0.296=11.6%

Thus the resulting probability for hypovolemic shock in this case is reduced from 39.4% to 11.6%, due to the high probability for cardiac shock.

In some situations, the determined unrestricted probability for hypovolemic shock (i.e. lack of blood volume in the circulation) can be utilized in fluid management for a patient, for example following an operation or at any time, and not only when a shock condition (low systolic blood pressure, high heart rate) is present. Lack of fluid prevents the heart from generating maximum cardiac output, while excess or high blood volume may cause lung edema. Once the unrestricted probability for hypovolemic shock ($P_{hypovolemic\ shock}$) has been determined as described in any of the embodiments above, a fluid status indicator (FluidDx) may be determined, for example:

Fluid Status=1−$P_{hypovolemic\ shock}$

If the determined FluidDx is low (i.e. hypovolemic shock probability is high), then the physician can supply fluid to the patient. Alternatively, if the fluid status indicator FluidDx is high (i.e. very low hypovolemic shock probability), this means that a condition of high blood volume may exist, which may lead to lung edema if not treated with appropriate medications. Thus, a monitor indicating a current FluidDx value may be a helpful addition to critical care, post-operative care or any hospital care environments. Any patient with a compromised circulation (that is, patient undergoing anesthesia, surgery, intensive care, chemo therapy and more) is in need of volume (or fluid) management. This is simply because common therapy has the goal to have the patient pump the highest stroke volume possible without causing lung edema (due to the inability of the heart of pumping the surplus of volume). Accordingly, the fluid status indicator is applicable to almost every patient. For hospital patients, a fluid status indicator may be provided in the form of a numerical value or a bar diagram, or in the form of a trend graph. A trend graph is particularly helpful for physician since a trend can be more useful than an absolute value of a critical patient parameter. For ER patients, the same fluid status indicator may be provided on a monitor or display screen in addition to shock indicators, also in the form of separate numerical values, bar diagrams, or trend graphs.

In one embodiment, a module for determining FluidDx may be included in the system of FIG. 1, where the decision systems may include a FluidDx generator which takes the unrestricted hypovolemic shock probability determined as described above and uses that probability to determine the fluid status indicator and provide that value as an output to a suitable output device such as output display unit 16. In this embodiment, the hypovolemic shock probability used in determining the fluid status indicator (i.e. patient blood volume) is not restricted by generic shock probability or any other type of shock, and is calculated whether the shock probability is low or high. This is because it is often important for physicians to know if a patient's fluid volume is high, low or normal, and to treat for high or low blood volume as soon as possible. Using the hypovolemic shock calculation above, where the unrestricted hypovolemic shock probability is 39.4%, so the fluid status indicator in this case is 60.6%. In an alternative embodiment, a FluidDx or blood volume monitoring unit may be provided as a stand-alone system for use in hospital care environments outside the emergency room, as described in more detail below in connection with FIGS. 17 and 18.

The example in Table 9 below considers probability for septic shock, using the following rules:

Rules for Parameter ICON (15% Weight)

RULE 1: IF IndexOfContractility IS increased THEN SepticShock_ICON IS probable;

RULE 2: IF NOT (IndexOfContractility IS increased) THEN SepticShock_ICON IS improbable;

Rules for Parameter SVR (35% Weight)

RULE 3: IF SystemicVascularResistance IS very_low THEN SepticShock_SVR IS probable;

RULE 4: IF NOT (SystemicVascularResistance IS very_low) THEN SepticShock_SVR IS improbable;

Rules with Parameter SVV (5% Weight)
(In alternative embodiments, the rules below may be changed to include the parameter FTc, as described above in connection with Table 4.)
RULE 5: IF StrokeVolumeVariation IS increased THEN SepticShock_SVV IS probable;
RULE 6: IF NOT (StrokeVolumeVariation IS increased) THEN SepticShock_SVV IS improbable;
Rules with Parameter CO (35% Weight)
RULE 7: IF CardiacOutput IS very_high THEN SepticShock_CO IS probable;
RULE 8: IF CardiacOutput IS high THEN SepticShock_CO IS possible;
RULE 9: IF (CardiacOutput IS normal) OR (CardiacOutput IS low) OR (CardiacOutput IS very_low) THEN SepticShock_CO IS improbable.
Rules with Parameter TFC (10% Weight)
RULE 10: IF ThoracicFluidContent IS increased THEN SepticShock_SVV IS probable;
RULE 11: IF NOT (ThoracicFluidContent IS increased) THEN SepticShock_SVV IS improbable.

Restriction factor for generic shock condition: $1-\mu'(P_{GS}, \text{"improbable"})=1-0=1$
Restriction factor by other shock cases (maximum of CS, HS): $1-\text{Max}(\mu'(P_{CS}, \text{"probable"}), \mu'(P_{HS}, \text{"probable"}))=1-0.704=0.296$
Restricted Septic Shock Probability: $P'(\text{shock}_{septic})=5.4\%$
Table 10 below is one example of a test case for processing an anaphylactic shock probability, using the following rules which correspond to Table 5 above:
Rules for Parameter SVR (45% Weight)
RULE 1: IF SystemicVascularResistance IS low THEN AnaphylacticShock_SVR IS probable;
RULE 2: IF NOT (SystemicVascularResistance IS low) THEN AnaphylacticShock_SVR IS improbable;
Rules for Parameter CO (45% Weight)
RULE 3: IF CardiacOutput IS increased THEN AnaphylacticShock_CO IS probable;
RULE 4: IF NOT (CardiacOutput IS increased) THEN AnaphylacticShock_CO IS improbable;
Rules with Parameter TFC (10% Weight)
(Note that rules for parameter TFC in anaphylactic shock evaluation may be eliminated in alternative embodiments, as described above in connection with FIG. 5).

TABLE 9

Evaluation for Septic Shock

| Param. | Normal Range | Value | Membership $\mu$(Value, Term) | Evaluation "Septic Shock" Probability $P_{Param}(\text{shock}_{septic})$ And Membership $\mu'$(P, Term) | Weight w |
|---|---|---|---|---|---|
| ICON | 38–62 | 20 | $\mu(20, \text{"very low"}) = 1$<br>$\mu(20, \text{"low"}) = 0$<br>$\mu(20, \text{"decreased"}) = 0$<br>$\mu(20, \text{"normal"}) = 0$<br>$\mu(20, \text{"increased"}) = 0$<br>$\mu(20, \text{"high"}) = 0$<br>$\mu(20, \text{"very high"}) = 0$ | $P_{ICON}(\text{shock}_{septic}) = 14.7\%$<br>$\mu'(P, \text{"improbable"}) = 0.706$<br>$\mu'(P, \text{"possible"}) = 0.294$<br>$\mu'(P, \text{"probable"}) = 0$ | 0.15 |
| SVR | 735–1225 | 1300 | $\mu(1300, \text{"very low"}) = 0$<br>$\mu(1300, \text{"low"}) = 0$<br>$\mu(1300, \text{"decreased"}) = 0$<br>$\mu(1300, \text{"normal"}) = 0.194$<br>$\mu(1300, \text{"increased"}) = 1$<br>$\mu(1300, \text{"high"}) = 0.806$<br>$\mu(1300, \text{"very high"}) = 0$ | $P_{SVR}(\text{shock}_{septic}) = 14.7\%$<br>$\mu'(P, \text{"improbable"}) = 0.706$<br>$\mu'(P, \text{"possible"}) = 0.294$<br>$\mu'(P, \text{"probable"}) = 0$ | 0.35 |
| SVV | 5–15 | 14 | $\mu(14, \text{"very low"}) = 0$<br>$\mu(14, \text{"low"}) = 0$<br>$\mu(14, \text{"decreased"}) = 0$<br>$\mu(14, \text{"normal"}) = 0.7$<br>$\mu(14, \text{"increased"}) = 1$<br>$\mu(14, \text{"high"}) = 0.30$<br>$\mu(14, \text{"very high"}) = 0$ | $P_{SVV}(\text{shock}_{septic}) = 85.2\%$<br>$\mu'(P, \text{"improbable"}) = 0$<br>$\mu'(P, \text{"possible"}) = 0.296$<br>$\mu'(P, \text{"probable"}) = 0.704$ | 0.05 |
| CO | 5.24–8.74 | 5.0 | $\mu(5.0, \text{"very low"}) = 0$<br>$\mu(5.0, \text{"low"}) = 0.639$<br>$\mu(5.0, \text{"decreased"}) = 1$<br>$\mu(5.0, \text{"normal"}) = 0.361$<br>$\mu(5.0, \text{"increased"}) = 0$<br>$\mu(5.0, \text{"high"}) = 0$<br>$\mu(5.0, \text{"very high"}) = 0$ | $P_{CO}(\text{shock}_{septic}) = 14.7\%$<br>$\mu'(P, \text{"improbable"}) = 0.706$<br>$\mu'(P, \text{"possible"}) = 0.294$<br>$\mu'(P, \text{"probable"}) = 0$ | 0.35 |
| TFC | 80–100 | 50 | $\mu(50, \text{"very low"}) = 1$<br>$\mu(50, \text{"low"}) = 0$<br>$\mu(50, \text{"decreased"}) = 0$<br>$\mu(50, \text{"normal"}) = 0$<br>$\mu(50, \text{"increased"}) = 0$<br>$\mu(50, \text{"high"}) = 0$<br>$\mu(50, \text{"very high"}) = 0$ | $P_{TFC}(\text{shock}_{septic}) = 14.7\%$<br>$\mu'(P, \text{"improbable"}) = 0$<br>$\mu'(P, \text{"possible"}) = 1$<br>$\mu'(P, \text{"probable"}) = 0$ | 0.10 |

Overall Shock Probability: $P(\text{shock}_{septic})=18.2\%$
Memberships of Probability: $\mu'(P_{SS}, \text{"improbable"})=0.636$
$\mu'(P_{SS}, \text{"possible"})=0.364$
$\mu'(P_{SS}, \text{"probable"})=0$ RULE 5: IF ThoracicFluidContent IS increased THEN SepticShock_SVV IS probable;
RULE 6: IF NOT (ThoracicFluidContent IS increased) THEN SepticShock_SVV IS improbable;

TABLE 10

Anaphylactic Shock Evaluation

| | | | | Evaluation "Anaphylactic Shock" | |
|---|---|---|---|---|---|
| Param. | Normal Range | Value | Membership μ(Value, Term) | Probability $P_{Param}(shock_{anaphylactic})$ And Membership μ'(P, Term) | Weight w |
| SVR | 735-1225 | 1300 | μ(1300, "very low") = 0<br>μ(1300, "low") = 0<br>μ(1300, "decreased") = 0<br>μ(1300, "normal") = 0.194<br>μ(1300, "increased") = 1<br>μ(1300, "high") = 0.806<br>μ(1300, "very high") = 0 | $P_{SVR}(shock_{anaphylactic})$ = 14.7%<br>μ'(P, "improbable") = 0.706<br>μ'(P, "possible") = 0.294<br>μ'(P, "probable") = 0 | 0.45 |
| CO | 5.24-8.74 | 5.0 | μ(5.0, "very low") = 0<br>μ(5.0, "low") = 0.639<br>μ(5.0, "decreased") = 1<br>μ(5.0, "normal") = 0.361<br>μ(5.0, "increased") = 0<br>μ(5.0, "high") = 0<br>μ(5.0, "very high") = 0 | $P_{TFC}(shock_{anaphylactic})$ = 14.7%<br>μ'(P, "improbable") = 0.706<br>μ'(P, "possible") = 0.294<br>μ'(P, "probable") = 0 | 0.45 |
| TFC | 80-100 | 50 | μ(50, "very low") = 1<br>μ(50, "low") = 0<br>μ(50, "decreased") = 0<br>μ(50, "normal") = 0<br>μ(50, "increased") = 0<br>μ(50, "high") = 0<br>μ(50, "very high") = 0 | $P_{TFC}(shock_{anaphylactic})$ = 14.7%<br>μ'(P, "improbable") = 0<br>μ'(P, "possible") = 1<br>μ'(P, "probable") = 0 | 0.10 |

Overall Shock Probability: $\overline{P(shock_{anaphylactic})}$=14.7%
Memberships of Probability: μ'($P_{AS}$, "improbable")= 0.706
  μ'($P_{AS}$, "possible")=0.294
  μ'($P_{AS}$, "probable")=0
Restriction factor for generic shock condition: 1−μ'($P_{GS}$, "improbable")=1−0=1
Restriction factor by other shock cases (maximum of CS, HS, SS): 1−Max(μ'($P_{CS}$, "probable"), μ'($P_{HS}$, "probable"), μ'($P_{SS}$, "probable"))=1−0.704=0.296
Restricted Anaphylactic Shock Probability: P'($shock_{anaphylactic}$)=4.4%

In the above example, cardiogenic shock is determined to be the most likely shock type, based on exemplary input parameter values. The following tables illustrate some case studies where hypovolemic shock, septic shock and anaphylactic shock, respectively, are determined to be probable using the above rules.

In the tables below, case studies where other types of shock are probable are provided. In the following tables, '−'=improbable, '+'=probable, '+/−'=possible, n/a=not applicable). The tables summarizes results for cases where generic shock is probable rather than improbable, and hypovolemic shock (Table 11), septic shock (Table 12) and anaphylactic shock (Table 13), respectively, are determined to be the most likely shock type.

Case Study—Probable Hypovolemic Shock

Table 11 below shows the results following the above rules with different values for the parameters, indicating likelihood of hypovolemic shock. This is a situation where there is a probability of a generic shock condition, so there is no restriction based on a generic shock improbable situation.

TABLE 11

Case Study for Hypovolemic Shock

| | Normal | | | Shock Evaluation | | | |
|---|---|---|---|---|---|---|---|
| Param. | Range | Value | Assignment | Cardiogenic | Hypovolemic | Septic | Anaphylactic |
| HR | 54-90 | 100 | increased (94.4%)<br>high (100%) | + | + | + | + |
| MAP | 80-100 | 50 | very low (100%) | + | + | + | + |
| ICON | 38-62 | 50 | normal (100%)<br>increased (50%) | − | +<br>+ | | n/a |
| SV | 77-128 | 70 | low (77.5%)<br>decreased (100%)<br>normal (22.5%) | +<br>− | + | n/a | n/a |
| STR | 0.3-0.5 | 0.30 | low (50%)<br>decreased (100%)<br>normal (50%) | −<br>− | +<br>+ | n/a | n/a |
| SVV | 5-15 | 30.0 | very high (100%) | − | + | − | n/a |
| SVR | 735-1225 | 1300 | normal (19.40%)<br>increased (100%)<br>high (80.6%) | + | + | − | − |

TABLE 11-continued

Case Study for Hypovolemic Shock

| Param. | Normal Range | Value | Assignment | Shock Evaluation Cardiogenic | Hypovolemic | Septic | Anaphylactic |
|---|---|---|---|---|---|---|---|
| TFC | 25-35 | 10 | very low (100%) | + | + | – | – |
| CO | 5.24-8.74 | 7.0 | decreased (49.4%) | n/a | n/a | | – |
| | | | normal (100%) | | | – | |
| | | | increased (50.6%) | | | | + |
| | Overall Shock Probability: | | | 45.1% | 85.2% | 21.4% | 34.1% |
| | After shock probability restriction: | | | 45.1% | 60.5% | 6.3% | 10.1% |

In this case, the probability for hypovolemic shock is the highest, and that probability is reduced by the cardiogenic shock probability, using equation 2 above. This results in a probability of 60.5% for hypovolemic shock.

Table 12 below shows the results following the above rules with different values for the parameters, indicating likelihood of septic shock. This is a situation where there is a probability of a generic shock condition, so there is no restriction based on a generic shock improbable situation. The following parameter set is typical for the septic shock, but some of the parameter values also meet the requirements for cardiogenic shock and hypovolemic shock. Thus the resulting probability in this case is reduced to 67.2%.

TABLE 12

Case Study for Septic Shock

| Param. | Normal Range | Value | Assignment | Shock Evaluation Cardiogenic | Hypovolemic | Septic | Anaphylactic |
|---|---|---|---|---|---|---|---|
| HR | 54-90 | 150 | very high (100%) | + | + | + | + |
| MAP | 80-100 | 50 | very low (100%) | + | + | + | + |
| ICON | 38-62 | 65 | normal (25%) | – | + | | n/a |
| | | | increased (100%) | | | + | |
| | | | high (75%) | – | + | | |
| SV | 77-128 | 120 | normal (81.4%) | – | | n/a | n/a |
| | | | increased (100%) | | – | | |
| | | | high (18.6%) | – | | | |
| STR | 0.3-0.5 | 0.15 | low (100%) | – | – | n/a | n/a |
| SVV | 5-15 | 14.0 | normal (70%) | | – | | n/a |
| | | | increased (100%) | + | | + | |
| | | | high (30%) | | +/– | | |
| SVR | 735-1225 | 100 | very low (100%) | – | – | + | – |
| TFC | 25-35 | 40 | increased (50%) | | | + | + |
| | | | high (100%) | – | – | | |
| CO | 5.24-8.74 | 18.0 | very high (100%) | n/a | n/a | + | – |
| | Shock Probability by rules: | | | 21.8% | 40.6% | 85.2% | 14.7% |
| | Shock probability after restriction: | | | 21.8% | 37.7% | 67.2% | 4.4% |

Table 13 below shows the results following the above rules with different values for the parameters, indicating likelihood of anaphylactic shock. The following parameter set is typical for the anaphylactic shock, but some of the parameter values are also indicator for a hypovolemic shock. Thus the resulting probability is reduced to 73.3%.

TABLE 13

Case Study for Anaphylactic Shock

| Param. | Normal Range | Value | Assignment | Shock Evaluation Cardiogenic | Hypovolemic | Septic | Anaphylactic |
|---|---|---|---|---|---|---|---|
| HR | 54-90 | 100 | increased (94.4%) | | | | |
| | | | high (100%) | + | + | + | + |
| MAP | 80-100 | 50 | very low (100%) | + | + | + | + |
| ICON | 38-62 | 35 | low (75%) | +/– | – | | n/a |
| | | | decreased (100%) | | | – | |
| | | | normal (25%) | – | + | | |
| SV | 77-128 | 90 | decreased (99.0%) | | + | n/a | n/a |
| | | | normal (81.4%) | – | | | |
| | | | increased (1.0%) | | – | | |
| STR | 0.3-0.5 | 0.15 | low (100%) | – | – | n/a | n/a |

TABLE 13-continued

Case Study for Anaphylactic Shock

| Param. | Normal Range | Value | Assignment | Shock Evaluation | | | |
|---|---|---|---|---|---|---|---|
| | | | | Cardiogenic | Hypovolemic | Septic | Anaphylactic |
| SVV | 5-15 | 5.0 | low (50%) | | – | | n/a |
| | | | decreased (100%) | – | | – | |
| | | | normal (50%) | | – | | |
| SVR | 735-1225 | 400 | low (100%) | – | – | – | + |
| | | | decreased (13.3%) | | | | |
| TFC | 25-35 | 40 | increased (50%) | | | + | + |
| | | | high (100%) | – | – | | |
| CO | 5.24-8.74 | 9.0 | normal (34.9%) | n/a | n/a | – | |
| | | | increased (100%) | | | | + |
| | | | high (65.1%) | | | +/– | |
| | Overall Shock Probability: | | | 26.7% | 30.8% | 26.3% | 85.2% |
| | After shock probability restriction: | | | 26.7% | 30.8% | 22.6% | 73.3% |

The system and methods described in the above embodiments generate probabilities of different types of shock. A filter may be applied to these probabilities which identifies the shock type with the highest probability as the most likely underlying shock type and ignores the other shock types.

The system and method described above may be modified to provide more details of shock conditions, such as sub-types of shock types or other shock types. Other embodiments of the system exchange the Fuzzy inference machine with a neural network or program instructions implementing suitable mathematic formulae to interpret input parameters.

Figure 14:
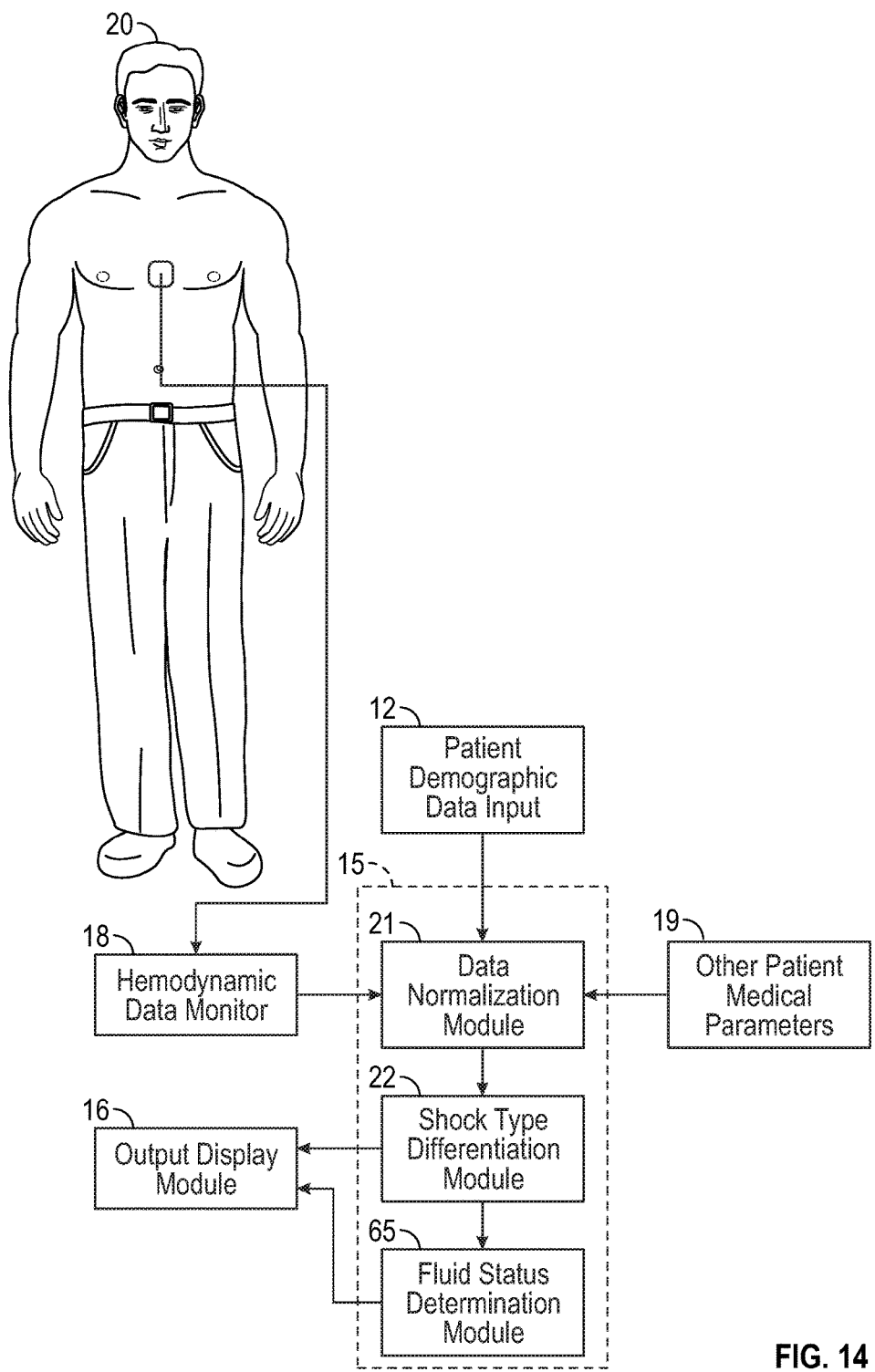
FIG. 14 is a block diagram of one embodiment of a real-time system for collecting hemodynamic data using a hemodynamic monitor and monitoring ongoing probability of different shock types based on the real-time data.

FIG. 14 is a block diagram illustrating one embodiment of a real-time system for collecting hemodynamic or other clinical data using a medical or hemodynamic monitor or the like and determining probability of different shock types, based on the real-time data and optionally also a fluid status indicator FluidDx derived from the hypovolemic shock probability. In this embodiment a hemodynamic or cardiac monitor 18 or the like is suitably connected to sensors attached to a patient 20, as illustrated in FIG. 14, and the output of monitor 18 is connected to an input of computer or processor 15 associated with data normalization module 21. Suitable hemodynamic monitors for this purpose are the ICON™ or AESCUILON™ monitors available from Osypka Medical, GmbH, Berlin, Germany, but other hemodynamic or other clinical parameter monitors may be used in other embodiments. Monitor 18 obtains clinical or hemodynamic parameter values which are output to the data normalization module. A patient demographic data input 12 is also connected to an input associated with data normalization module 21. A clinical or medical data collection module 19 for input of other patient clinical parameters including respiration rate or ventilation rate, body temperature, flow time, or the like is also connected to the data normalization module 21. Module 19 or processor 15 may also be programmed to determine parameters derived from collected hemodynamic or clinical values using linear or nonlinear statistics. For example, heart rate complexity (HRC), scientifically referred to as the sample entropy of heart rate, is a clinical parameter or vital sign used in critical care medicine which is derived from selected cardiac parameters based on non-linear statistics. Shock type differentiation module 22 determines the probability of different shock types as described above, and the results are input to display module 16. The hypovolemic shock probability is also provided as an output to the fluid status determination module 65 in one embodiment, and the fluid status index is determined as described above in connection with FIG. 3 and provided as an input to display module 16.

One or more of the data normalization module 21, shock type differentiation module 22 and fluid status determination module 65 in this embodiment may be integrated into the hemodynamic monitor. The output display module 16 may also be integral with the hemodynamic monitor, i.e. output shock probabilities may be displayed on the existing hemodynamic monitor output data screen.

Figure 15:
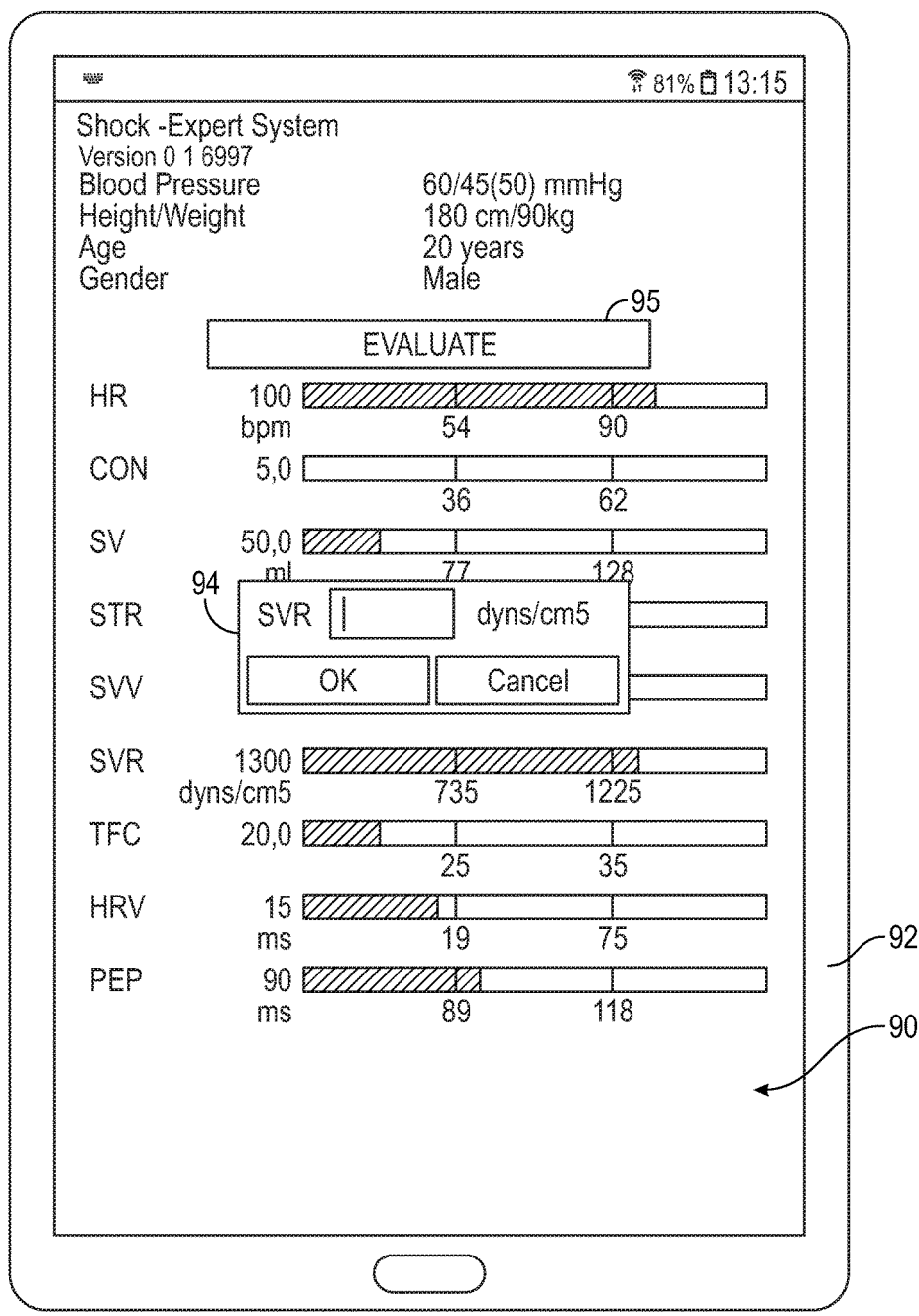
FIG. 15 is a screen shot illustrating a clinical and demographic data input page of one embodiment of a smart phone application or website for differentiating different shock type probabilities.
Figure 16:
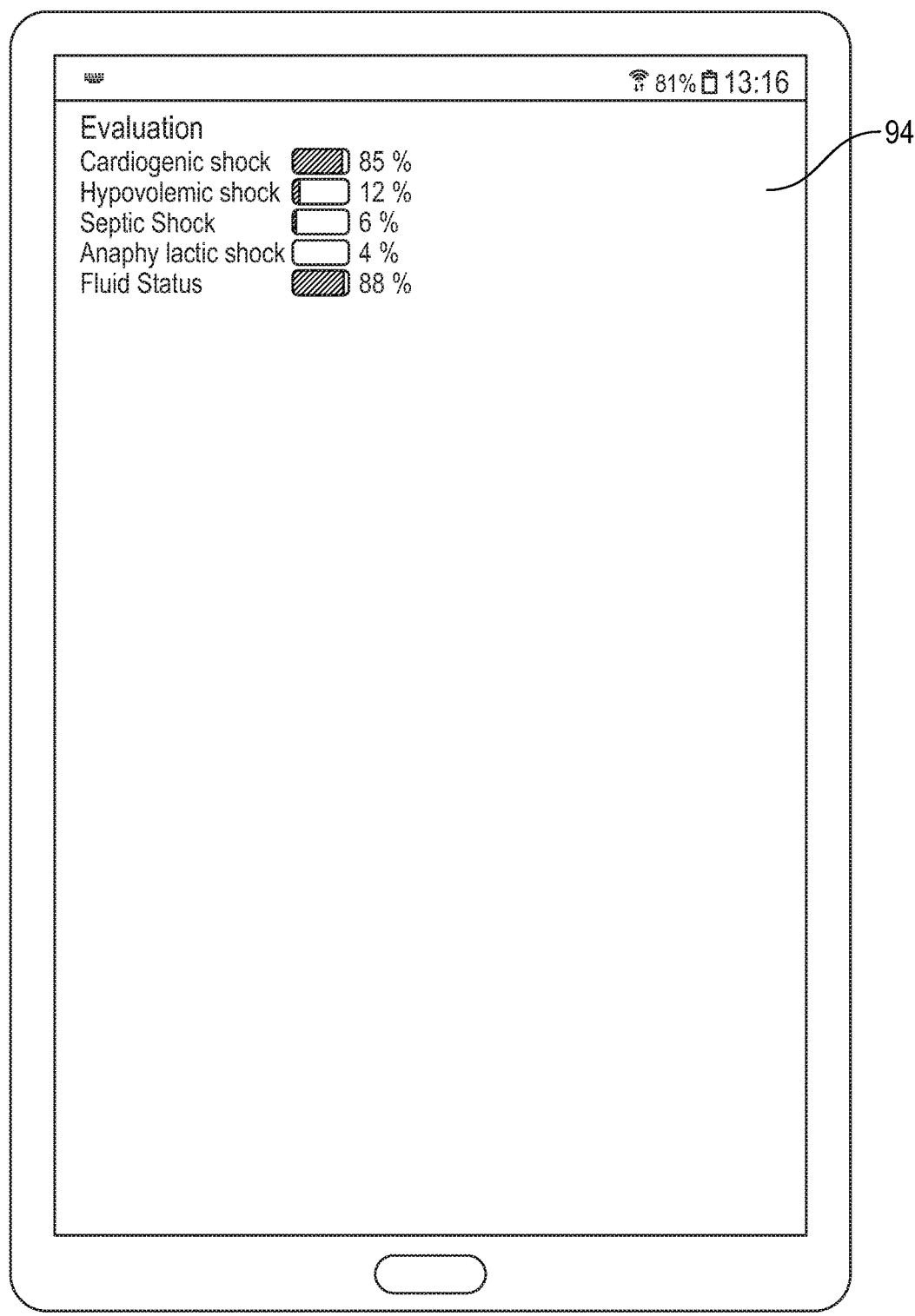
FIG. 16 is a screen shot illustrating a display of probabilities of different shock types as well as a fluid status indicator determined by the system and method of FIGS. 1 to 15 in one embodiment of a smart phone application or website.

FIGS. 15 and 16 illustrate an embodiment of the system and method described above employed as a smart phone application ('app'). With no direct automatic access to the patient's demographic data and clinical or hemodynamic parameter values or derived values via a monitoring device, as is sometimes the case in an emergency situation, this data may be entered manually on a data entry screen 90 provided on a shock differentiator app which may installed on a smart phone 92 as illustrated in FIG. 15 or another portable user device such as a laptop or tablet computer. The user clicks on a parameter (in this case SVR) and a pop up window 94 appears for entry of the measured value. A similar pop up window is provided on clicking each of the parameters in FIG. 15. A similar screen is provided for entry of demographic data for a patient undergoing a shock evaluation. Once all data is entered, the user clicks on the tab 95 "Evaluate", and the results 97 are computed and displayed on result display screen 96 (FIG. 16). FIG. 16 illustrates one possible presentation of the results, that is, the probabilities for the different shock types. In some embodiments, a fluid status indicator determined based on the unrestricted hypovolemic shock probability may also be displayed, when that option is included in the system and method described above. In this embodiment, the results are displayed as numeric percentages as well as in bar chart form. In alternative embodiments, they may alternatively be displayed as a trend graph over time.

Figure 17:
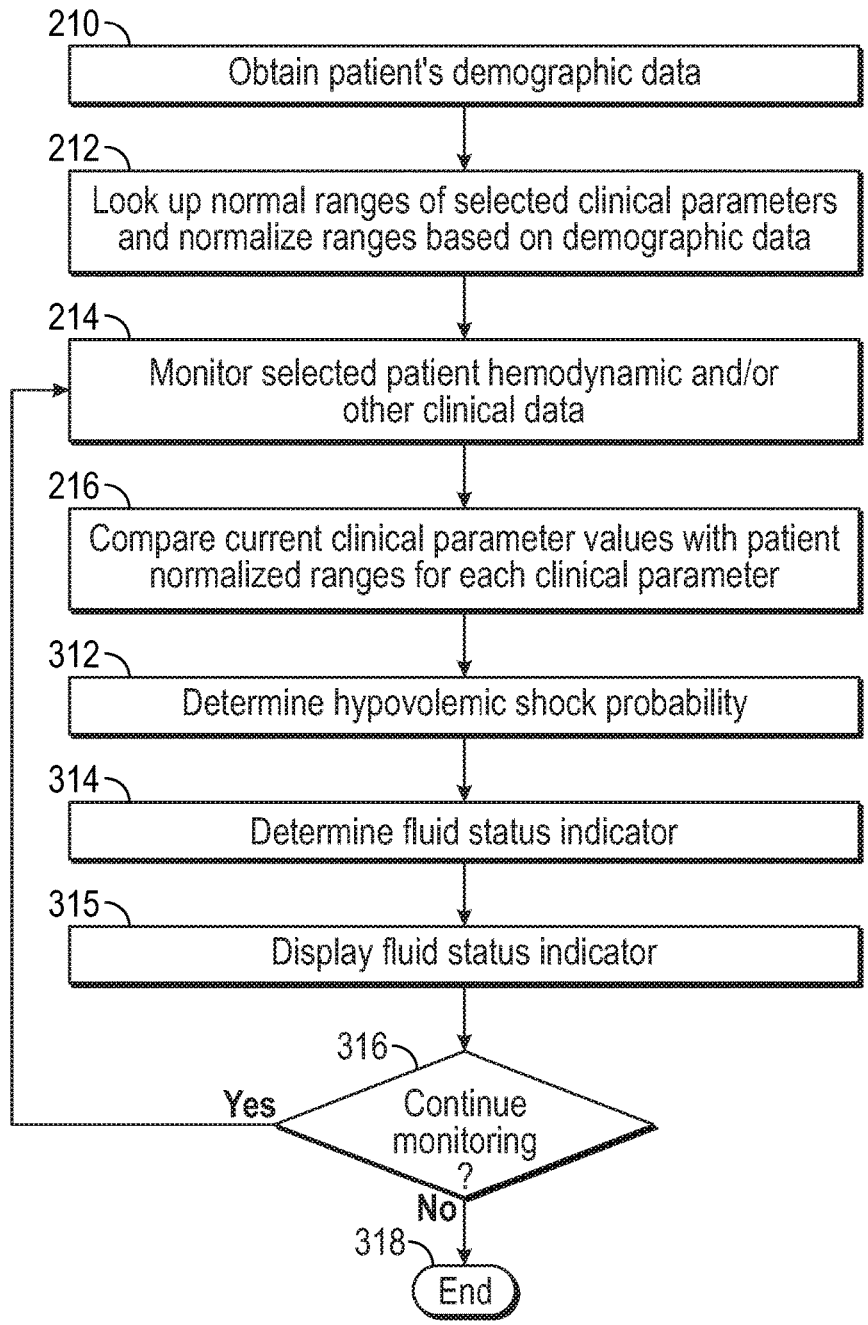
FIG. 17 is a flow diagram illustrating one embodiment of method of determining a blood volume or fluid data indicator using an unrestricted hemodynamic shock probability.
Figure 18:
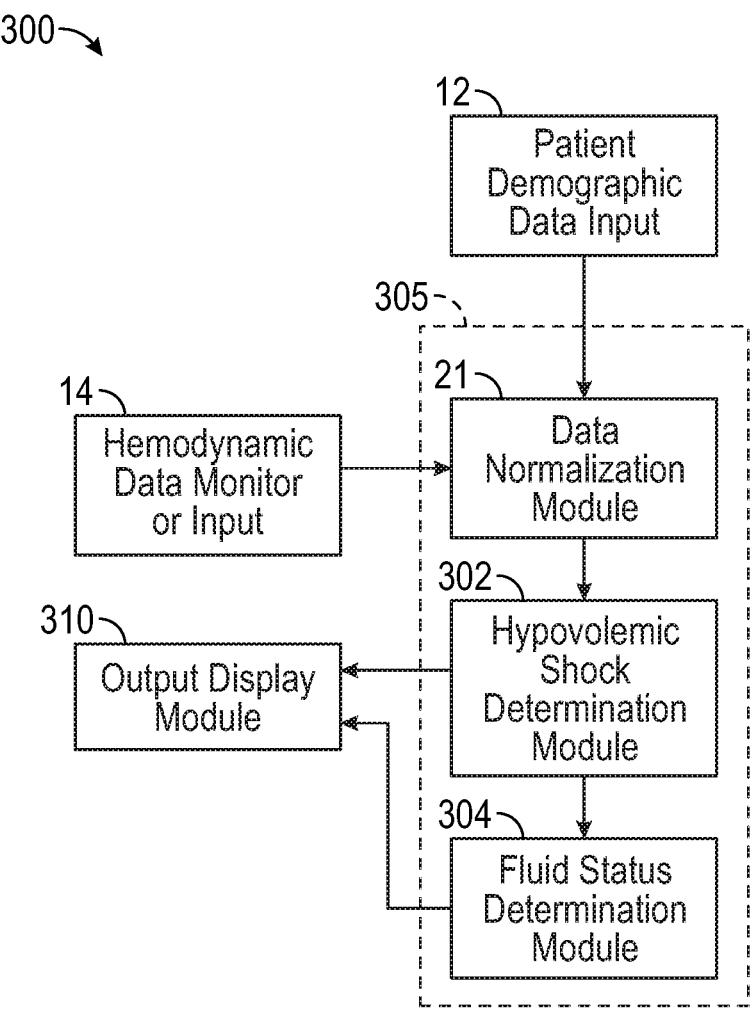
FIG. 18 is a block diagram of one embodiment a fluid data or blood volume monitoring system using the method of FIG. 17.

FIGS. 17 and 18 illustrate one embodiment of a method and system for determining and monitoring a patient's fluid data or blood volume, using parts of the shock differentiation system of the previous embodiments, specifically the determination of an unrestricted hypovolemic shock probability. The fluid indicator or blood volume monitoring system 300 illustrated in FIG. 18 may be used in hospital care environments outside the emergency room or in the emergency room or other emergency medical care situations where other means are used to determine shock type and treat a patient. In some situations, the determined unrestricted probability for hypovolemic shock (i.e. lack of blood volume in the circulation) can be utilized in fluid management for a patient, for example following an operation or at any time, and not only when a shock condition (low systolic blood pressure, high heart rate) is present. Some shock treatments and other medical treatments can themselves lead to low or high fluid levels, making the use of such a monitor desirable in an emergency situation as well as for monitoring and managing fluid levels in a hospital patient. Lack of fluid prevents the heart from generating maximum cardiac output, while excess or high blood volume may cause lung edema.

Some modules of the system of FIG. 18 and some steps of the method of FIG. 17 are identical to modules and steps of the shock differentiation system and method of FIGS. 1 and 2, and like reference numbers are used for like parts and steps as appropriate. As illustrated in FIG. 18, the fluid data or blood volume monitoring system 300 comprises at least one computer or processor 305 having an input 12 for a patient's demographic and any other relevant data, one or more inputs 14 for receiving clinical data such as hemodynamic or other data for determining probability of hypovolemic shock, and an output module or output display unit 310 for displaying a determined fluid status indicator (FluidDx). Processor or hardware processing unit 305 basically comprises a data processing/normalization module 21, a hypovolemic shock determination module 302, and a fluid status determination module 304.

FIG. 17 is a flow diagram illustrating one embodiment of a method which may be implemented on processor 305 for determining a fluid status indicator. In step 210, demographic data for a patient in emergency care or in a hospital or under regular medical care of any sort is obtained either directly or from patient records. In step 212, normal ranges of selected clinical parameters are retrieved from a local or remote data base, and the ranges are normalized based on the patient's demographic data. In step 214, selected clinical data (such as the parameters described above for determining hypovolemic shock probability) is input by medical personnel or monitored using a suitable monitor hooked up to the patient, continuously or at selected time intervals. In step 216, the currently input patient clinical parameters are compared with normalized ranges for the respective parameters as determined in step 212.

In step 312, an unrestricted hypovolemic shock probability is determined. This determination may be made using a method similar to the method described above and illustrated in FIG. 12 for unrestricted cardiogenic shock determination, with different weightings applied to individual parameter based probabilities for the clinical parameters used in the determination of hypovolemic shock. The unrestricted hypovolemic shock probability may be determined as described above in connection with Tables 3 and 8. Once the current unrestricted probability for hypovolemic shock ($P_{hypovolemic\ shock}$) has been determined (step 312), a fluid status indicator (FluidDx) is determined in step 314, using the relationship: Fluid Status=$1-P_{hypovolemic\ shock}$ The fluid status indicator in step 315 is then displayed on a suitable output device, such as a display unit on the monitor itself, or a remote display unit on a mobile device, tablet, or other computer, or on a desktop computer screen. The fluid status indicator may also be stored in a suitable data storage module. If the determined FluidDx is low (i.e. hypovolemic shock probability is high), then the physician can supply fluid to the patient. Alternatively, if the fluid status indicator FluidDx is high (i.e. very low hypovolemic shock probability), this means that a condition of high blood volume may exist, which may lead to lung edema if not treated with appropriate medications. In one embodiment, the FluidDx is monitored over time to provide updated outputs periodically, to determine whether treatment is going in the right direction. Thus, steps 214 to 316 are repeated as long as monitoring is to be continued (step 316) until the monitor or screen is turned off, at which point processing ends at step 318 and can be re-started as needed for the same or different patients. Thus, a stand-alone monitor or other display screen indicating a current FluidDx value may be a helpful addition to critical care, post-operative care or any hospital care environments. Any patient with a compromised circulation (that is, patient undergoing anesthesia, surgery, intensive care, chemo therapy and more) is in need of volume (or fluid) management. This is because the goal of therapy is to have the patient pump the highest stroke volume possible without causing lung edema (due to the inability of the heart of pumping the surplus of volume). Accordingly, the fluid status indicator is applicable to almost every patient. For hospital patients, a fluid status indicator may be provided in the form of a numerical value or a bar diagram, or in the form of a trend graph. A trend graph is particularly helpful for physician since a trend can be more useful than an absolute value of a critical patient parameter. For ER patients, the same fluid status indicator may be provided on a monitor or display screen in addition to shock indicators, also in the form of separate numerical values, bar diagrams, or trend graphs. In some embodiments, the unrestricted hypovolemic shock probability may also be displayed.

Figure 19:
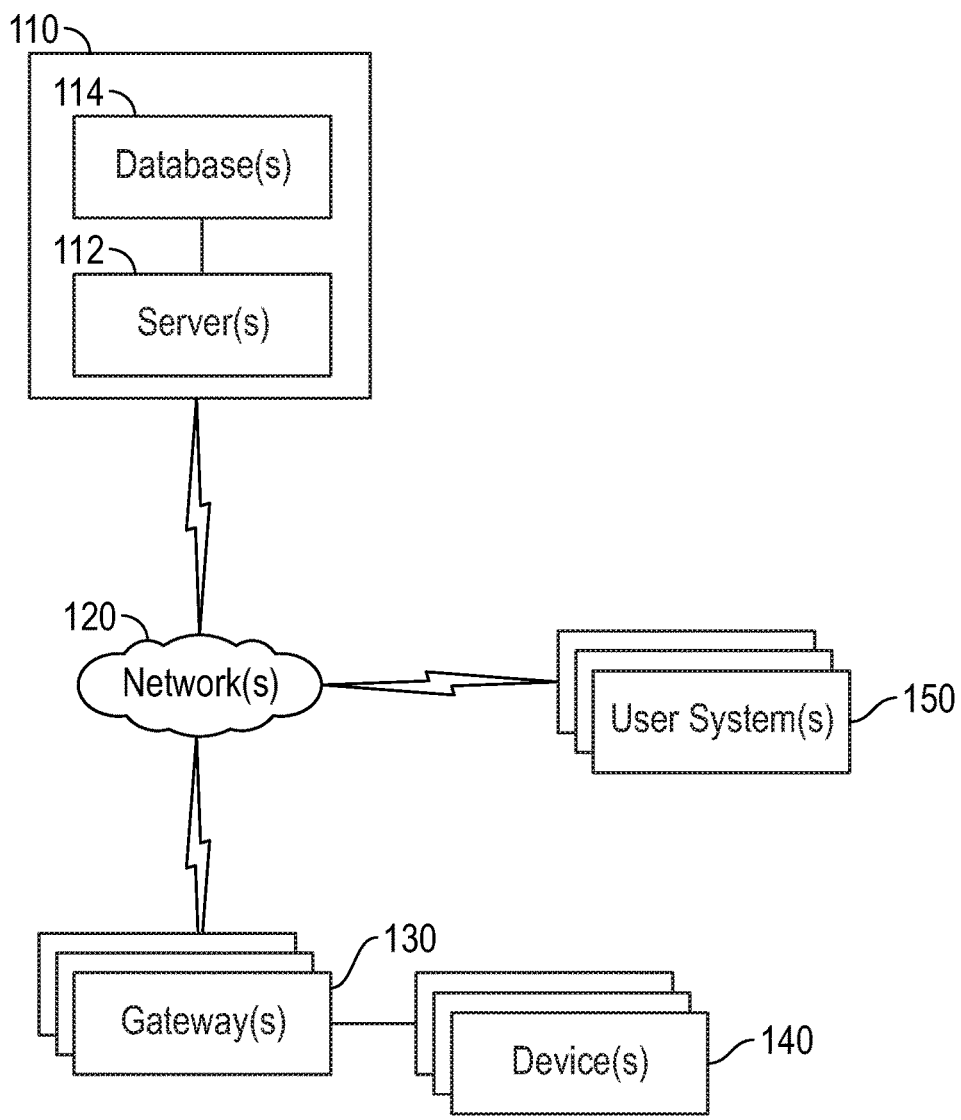
FIG. 19 illustrates an embodiment in which the shock decision or shock type probability determining system of FIGS. 1 to 16 is embodied in a network based system.

FIG. 19 illustrates an embodiment of a system in which the shock decision or shock type probability determining system of FIGS. 1 to 16 or the fluid status indicator or monitor of FIGS. 17 and 18 is embodied in a remote system or website 110 accessible using various user devices 140 or systems 150 such as a desktop, laptop, smart phone or pad computer or the like via the Internet or other network 120. The user device of FIGS. 15 and 16 may communicate with a remote website 110 as in FIG. 17 in one embodiment, or may be a stand-alone shock probability determination system which incorporates one or more processors, software and database(s) for computing shock and/or fluid status indicators based on physician or medical personnel input and other data.

The distributed, network-based system 110 of FIG. 19 may comprise a set of one or more servers 112 (also referred to herein as a "platform") which host and/or execute one or more of the various functions, processes, and/or modules described herein. Servers 112 may be associated with one or more local or remote database(s) 114. In addition, server(s) 112 may be communicatively connected to one or more gateway(s) 130 and one or more user systems or devices 140, 150 via one or more network(s) 120. Network(s) 120 may comprise the Internet, and server(s) 112 may communicate with gateway(s) 130 and user system(s) or device(s) 140, 150 through the Internet using standard transmission protocols, such as HyperText Transfer Protocol (HTTP), Secure HTTP (HTTPS), File Transfer Protocol (FTP), FTP Secure (FTPS), SSH FTP (SFTP), and the like, as well as proprietary protocols. In an embodiment, server(s) 112 may not be dedicated servers, and may instead be cloud instances, which utilize shared resources of one or more servers. It should also be understood that server(s) 112 may be, but are not required to be, collocated. Furthermore, while server(s) 112 are illustrated as being connected to various systems through a single set of network(s) 120, it should be understood that the server(s) 112 may be connected to the various systems via different sets of one or more networks. For example, server(s) 120 may be connected to a subset of user systems 150 and gateways 130 and user devices 140 via the Internet, but may be connected to one or more other user systems 150 or devices 140 via an intranet, for example via a hospital or medical center intranet. It should also be understood that user systems or devices 150, 140 may comprise any type or types of computing devices capable of wired and/or wireless communication, including without limitation, desktop computers, laptop computers, tablet computers, smart phones or other mobile phones, servers, electronic kiosks, and the like. In some embodiments, the device(s) 140 may be incorporated in patient monitoring devices such as hemodynamic monitors as described above in connection with FIG. 14 which collect clinical or hemodynamic data from a patient for transmission to the website 110 via network(s) 120. In addition, while only a few user systems 140, 150 and one set of server(s) 112 are illustrated, it should be understood that the network may comprise any number of user systems and sets of server(s).

Platform 112 may comprise web servers which host one or more websites or web services. In embodiments in which a website is provided, the website may comprise one or more user interfaces, including, for example, webpages generated in HyperText Markup Language (HTML) or other language. Platform 112 transmits or serves these user interfaces in response to requests from user system(s) 150 and devices 140. In some embodiments, these user interfaces may be served in the form of a wizard, in which case two or more user interfaces may be served in a sequential manner, and one or more of the sequential user interfaces may depend on an interaction of the user or user system with one or more preceding user interfaces. The requests to platform 112 and the responses from platform 112, including the user interfaces, may both be communicated through network(s) 120, which may include the Internet, using standard communication protocols (e.g., HTTP, HTTPS). These user interfaces or web pages may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases 114 that are locally and/or remotely accessible to platform 112. Platform 112 may also respond to other requests from user system(s) 150 and device(s) 140.

Platform 112 may further comprise, be communicatively coupled with, or otherwise have access to one or more database(s). For example, platform 112 may comprise one or more database servers which manage one or more databases. A user system 150 or application executing on platform 112 may submit data (e.g., user data, form data, etc.) to be stored in the database(s), and/or request access to data stored in such database(s). Any suitable database may be utilized, including without limitation MySQL™, Oracle™, IBM™, Microsoft SQL™, Sybase™, Access™, and the like, including cloud-based database instances. Data may be sent to platform 112, for instance, using the well-known POST request supported by HTTP, via FTP, etc. This data, as well as other requests, may be handled, for example, by server-side web technology, such as a servlet or other software module, executed by platform 112.

In embodiments in which a web service is provided, platform 112 may receive requests from user device(s) and system(s) 150, and provide responses in eXtensible Markup Language (XML) and/or any other suitable or desired format. In such embodiments, platform 112 may provide an application programming interface (API) which defines the manner in which user system(s) 150 and devices 140 may interact with the web service. Thus, user system(s) 150, which may themselves be servers, can define their own user interfaces, and rely on the web service to implement the backend processes, functionality, storage, etc., described herein. For example, in such an embodiment, a client application executing on one or more user system(s) 150 may interact with a server application executing on platform 112 to execute one or more or a portion of one or more of the various functions, processes, and/or software modules described herein. The client application may be "thin," in which case processing is primarily carried out server-side by platform 112. A simple example of a thin client application is a browser application, which simply requests, receives, and renders web pages at user system(s) 150 or device(s) 140, while platform 112 is responsible for generating the web pages and managing database functions. Alternatively, the client application may be "thick," in which case processing is primarily carried out client-side by user system(s) 150 and device(s) 140. For example, server(s) 112 may simply comprise database server(s) which provide storage and database management functions, while user system(s) 140 and device(s) 150 provide all of the other disclosed functionality. It should be understood that the client application may perform an amount of processing, relative to platform 112, at any point along this spectrum between "thin" and "thick," depending on the design goals of the particular implementation. In any case, the application, which may wholly reside on either platform 112 or user system(s) 150/devices 140, or be distributed between platform 112 and user system(s) 150 and devices 140, can comprise one or more executable software modules that implement one or more of the processes or functions of the application(s) described herein.

In an alternative embodiment to the network-based system illustrated in FIG. 19, the processes discussed herein may be implemented as a stand-alone application that may reside and be executed or otherwise utilized on a single user device, such as a desktop computer or mobile device (e.g., tablet computer, smart phone, etc.). In such an embodiment, all data may be stored and processed locally on the device. However, it should be understood that, even in such stand-alone embodiments, the application may be downloaded and updated from server(s) 112 via network 120.

It should be further understood that any of the data described herein as being accessed, retrieved, stored, etc. may reside on a database of user system(s) 150 and/or devices 140 and/or a database 114 of server(s) 112 and may be accessed by modules of user system(s) 150 and devices 140, modules of server(s) 112, or modules of user system(s) 150 and devices 140 as well as server(s) 112. For instance, in embodiments in which the application comprises a stand-alone application executing on a user system 150 or device 140, or on server(s) 112, application modules may store and access data in a local memory of a user system 150, a user device 140, or server(s) 112, respectively. As another example, in embodiments in which the application comprises a distributed application, application modules of a client application on a user system 150 or device 140 or may store and/or access data in a remote memory of server(s) 112 (e.g., via network(s) 120) and/or in a local memory of user system 150 or device 140.

Those of skill will appreciate that the various illustrative logical blocks, units, modules, circuits, and algorithm steps described in connection with the embodiments disclosed herein can often be implemented as electronic hardware, computer software, or combinations of both. To clearly illustrate this interchangeability of hardware and software, various illustrative components, units, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block or step is for ease of description. Specific functions or steps can be moved from one module or block without departing from the invention.

The various illustrative logical blocks, components, units, and modules described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Figure 20:
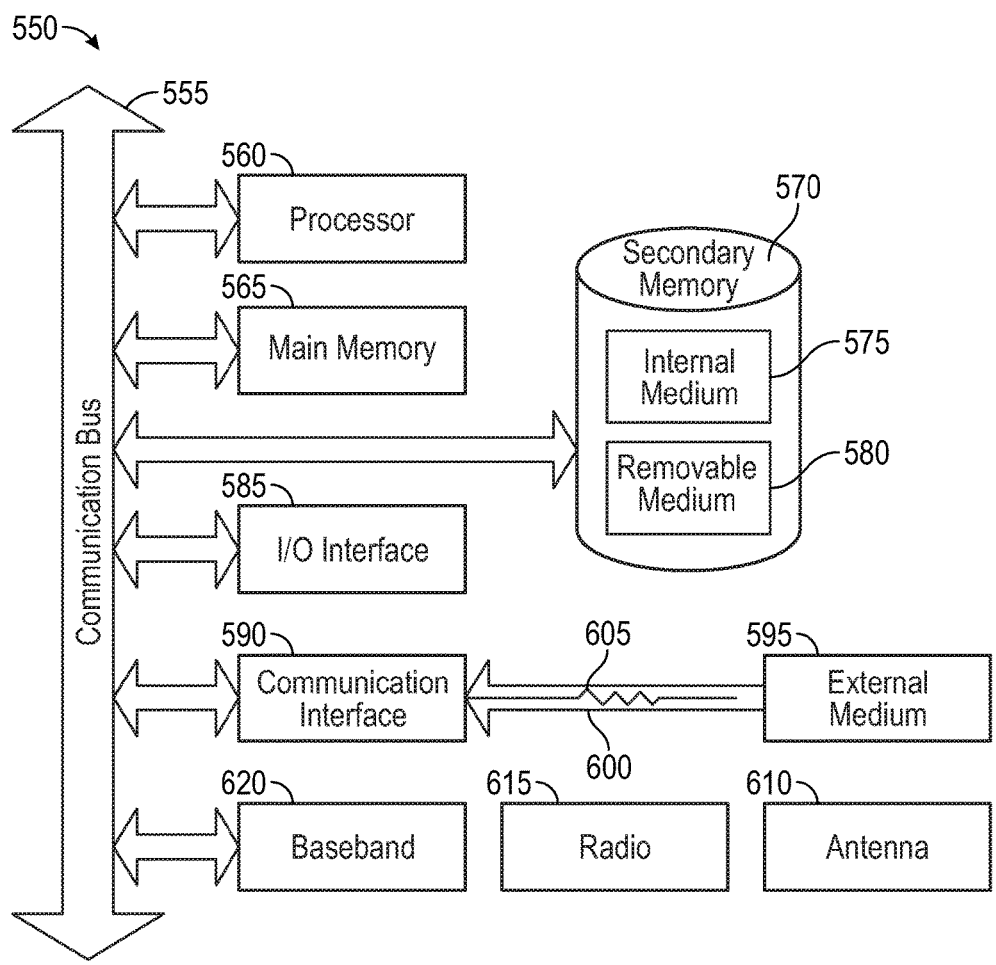
FIG. 20 illustrates a processing system on which one or more of the processes described herein may be executed, according to an embodiment.

FIG. 20 is a block diagram illustrating an example wired or wireless system 550 that can be used in connection with various embodiments described herein. For example the system 550 can be used as or in conjunction with one or more of the mechanisms or processes described above, and may represent components of system 10, the corresponding backend server(s), and/or other devices described herein. The system 550 can be a combination of one or more of the following: a server or any conventional personal computer, or any other processor-enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7® processor, and Xeon® processor, all of which are available from Intel Corporation of Santa Clara, Calif.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Pearl, Visual Basic, .NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, voice input, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 610, a radio system 615 and a baseband system 620. In the system 550, radio frequency (RF) signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit (IC). The demodulator and modulator can also be separate components. In the incoming path, the demodulator strips away the RF carrier signal leaving a baseband receive signal, which is sent from the radio system 615 to the baseband system 620.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application, or an Internet or cloud service.

The above description of the disclosed embodiments is provided to enable any person skilled in the art to make or use the invention. Various modifications to the disclosed embodiments will be readily apparent to those skilled in the art, and the generic principles defined herein can be applied to other embodiments without departing from the spirit or scope of the invention. Thus, the invention is not intended to be limited to the embodiments shown herein but is to be accorded the widest scope consistent with the principles and novel features disclosed herein. It is further understood that the scope of the present invention fully encompasses other embodiments that may become obvious to those skilled in the art and that the scope of the present invention is accordingly limited by nothing other than the appended claims.

We claim:

1. A computer implemented method of determining shock probabilities for a plurality of shock types, wherein one or more computing devices comprising data storage and a hardware processor are programmed to perform steps comprising, during treatment of a patient by a healthcare provider:
    receiving or retrieving demographic data of the patient undergoing treatment;
    receiving input of a plurality of currently measured values of selected variable clinical parameters of the patient, comprising at least hemodynamic parameters, from a hemodynamic monitor connected to the patient;
    comparing each clinical parameter value to a normal range for that parameter based on input or stored patient demographic data;
    determining probabilities of two or more shock types comprising at least cardiogenic shock and hypovolemic shock using some or all of the clinical parameter values relative to the normal range for the respective parameter values, wherein selected groups of clinical parameters are assigned to the respective shock types for determining the shock probability;
    displaying a shock probability for each shock type on an output display unit;
    determining a patient's fluid status indicator FluidDx=1−$P_{HYPO}$, where $P_{HYPO}$ is the hypovolemic shock probability; and
    displaying the fluid status indicator on the output display device and periodically updating the fluid status indicator during the treatment of the patient, so as to alert the healthcare provider to supply fluid to the patient or treat a condition of high blood volume based on a level of the fluid status indicator.

2. A system for determining probabilities of a plurality of different shock types based on patient clinical parameters, the system comprising:
    a non-transitory computer readable medium configured to store executable programmed modules;
    a processor communicatively coupled with the non-transitory computer readable medium and configured to execute programmed modules stored therein;
    an output display unit; and
    one or more programmed modules stored in the non-transitory computer readable medium and configured to be executed by the processor, the one or more programmed modules configured to, during treatment of a patient by a healthcare provider:
        receive or retrieve demographic data of the patient undergoing treatment;
        receive input of a plurality of currently measured values of selected clinical parameters of the patient, comprising at least hemodynamic parameters, from a hemodynamic monitor connected to the patient;
        assign selected groups of clinical parameters to respective different shock types;
        compare each currently measured clinical parameter value to a normal range for that parameter based on determined or stored patient demographic data;
        determine probabilities of the respective different shock types based on the comparison of each current clinical parameter value in the respective group to the normal range for the respective clinical parameter; and
        display a shock probability for each shock type on an output display unit,
    wherein the one or more programmed modules are further configured to determine a generic shock probability M (generic shock condition "improbable") using at least two selected clinical parameters indicative of any type of shock condition being present, and to compute a restricted probability of at least some shock types based on the determined generic shock probability if M(generic shock condition "improbable") is greater than zero according to the following:

$$P^*(\text{shock type}) = P(\text{shock type}) * (1 - M(\text{generic shock condition, 'improbable'})),$$

where P*(shock type)=restricted shock probability due to a generic shock condition 'improbable', and P(shock type)=unrestricted probability of the respective shock type prior to generic shock restriction,
    where one of the shock types is hypovolemic shock, and
    wherein the one or more programmed modules are further configured to determine a patient's fluid status indicator FluidDx=1−$P_{HYPO}$, where $P_{HYPO}$ is the unrestricted hypovolemic shock probability, display the fluid status indicator on the output display device, and periodically update the fluid status indicator during treatment of the patient, so as to alert the healthcare provider to supply fluid to the patient or treat a condition of high blood volume based on a level of the fluid status indicator.

3. The system of claim 2, wherein the one or more programmed modules are further configured to determine updated shock probabilities and an updated fluid status indicator at periodic intervals based on changes in the input clinical parameter values over time, and to display updated shock probabilities and fluid status indicators on the output display device in the form of one or more of numeric values, a bar chart and a trend graph illustrating variation in the probability of each shock type and the fluid status indicator over time.

4. A system for monitoring a patient's fluid status indicator for fluid management, the system comprising:
    a non-transitory computer readable medium configured to store executable programmed modules;
    a processor communicatively coupled with the non-transitory computer readable medium and configured to execute programmed modules stored therein;
    an output display unit; and
    one or more programmed modules stored in the non-transitory computer readable medium and configured to be executed by the processor, the one or more programmed modules configured to, during treatment of a patient by a healthcare provider:

receive demographic data or retrieve stored demographic data of a patient undergoing treatment;

receive input of a plurality of currently measured values of selected variable clinical parameters of the patient, comprising at least hemodynamic parameters, from a hemodynamic monitor connected to the patient, the clinical parameters being selected for determining a current probability of hypovolemic $P(shock_{hypovolemic})$;

compare each received clinical parameter value to a normal range for that parameter based on input or stored patient demographic data;

determine the probability of hypovolemic shock based on the comparison of each received clinical parameter value with the normal range for the respective clinical parameter;

determine a fluid status indicator FluidDx indicative of blood volume from the following relationship: $FluidDx=1-P(shock_{hypovolemic})$; and display the fluid status indicator on the output display unit and periodically update the fluid status indicator during the treatment of the patient, so as to alert the healthcare provider to supply fluid to the patient or treat a condition of high blood volume based on a level of the fluid status indicator.

5. The system of claim 4, wherein the programmed modules are further configured to monitor the selected clinical parameter values, to determine updated probabilities of hypovolemic shock and updated fluid status indicators on an ongoing basis based on current clinical parameter values, and to display updated fluid status parameters on the output display unit, wherein the output display comprises one or more of a numeric display, a bar chart, and a trend graph illustrating variation in the fluid status parameter over time.

* * * * *